(12) United States Patent
Hangya et al.

(10) Patent No.: US 12,171,653 B2
(45) Date of Patent: Dec. 24, 2024

(54) FOLDING DEVICE AND INJECTOR SYSTEM FOR INTRAOCULAR LENSES

(71) Applicant: MEDICONTUR MEDICAL ENGINEERING LTD., Zsambek (HU)

(72) Inventors: Peter Hangya, Bicske (HU); Laszlo Kontur, Budapest (HU)

(73) Assignee: MEDICONTUR MEDICAL ENGINEERING LTD., Zsambek (HU)

( * ) Notice: Subject to any disclaimer, the term of this patent is extended or adjusted under 35 U.S.C. 154(b) by 834 days.

(21) Appl. No.: 17/183,237

(22) Filed: Feb. 23, 2021

(65) Prior Publication Data

US 2021/0186683 A1    Jun. 24, 2021

Related U.S. Application Data

(63) Continuation-in-part of application No. 16/958,317, filed as application No. PCT/HU2017/000053 on Dec. 28, 2017, now abandoned.

(51) Int. Cl.
*A61F 2/16*    (2006.01)

(52) U.S. Cl.
CPC ............ *A61F 2/1678* (2013.01); *A61F 2/167* (2013.01)

(58) Field of Classification Search
CPC ............... A61M 5/20; A61M 5/31501; A61M 5/31595; A61M 2005/202; A61M 2005/2086; A61M 2005/3115; A61M 2005/3143; A61F 2/1662; A61F 2/1664; A61F 2/1667; A61F 2/167; A61F 2/1672; A61F 2/1675; A61F 2/1678; A61F 2/1691; A61F 2002/1681; A61F 2002/1682; A61F 2002/1683; A61F 2002/1686; A61F 2002/1689; A61F 2002/169; A61F 2002/16901; A61F 2002/16902; A61F 2002/16903; A61F 2002/16905; A61F 2002/169051; A61F 2002/169052;

(Continued)

(56) References Cited

U.S. PATENT DOCUMENTS 4,681,102 A * 7/1987 Bartell .................. A61F 2/1678 606/1
5,803,925 A * 9/1998 Yang ..................... A61F 2/1664 606/107

(Continued)

FOREIGN PATENT DOCUMENTS

DE    102006000929 A1    7/2007
EP        2286762 A1    2/2011

(Continued)

*Primary Examiner* — Kankindi Rwego
(74) *Attorney, Agent, or Firm* — Olson & Cepuritis, Ltd.

(57) ABSTRACT

An injection system for an intraocular lens (IOL) utilizes a folding device for the IOL. The folding device comprises a pair of co-acting winglets pivotable between an open position and a closed position, and together defining a hinge axis and a receptacle for the IOL. Each winglet has an outwardly extending, unitary leg portion defining a base plane that includes the hinge axis and a motion limiting protuberance on each said leg portion extending from the base plane. The base planes are situated at an angle relative to one another and the protuberances abut one another when the winglets are in the open position. The base planes merge into a single plane when the winglets are in the closed position.

16 Claims, 17 Drawing Sheets

(58) Field of Classification Search
CPC ............ A61F 2002/169053; A61B 5/150106; A61B 5/150137; A61B 5/150167; A61B 5/15019; A61B 5/150198; A61B 5/150206; A61B 5/150259; A61B 5/15103; A61B 5/15105; A61B 5/15107; A61B 5/15192; A61B 5/15198
USPC .............................................. 623/6.11, 6.12
See application file for complete search history.

(56) References Cited

U.S. PATENT DOCUMENTS

| | | | |
|---|---|---|---|
| 5,947,975 A * | 9/1999 | Kikuchi | A61F 2/1664 606/107 |
| 7,156,854 B2 | 1/2007 | Brown et al. | |
| 2002/0103490 A1 * | 8/2002 | Brady | A61F 2/1664 606/107 |
| 2004/0199174 A1 * | 10/2004 | Herberger | A61F 2/1678 606/107 |
| 2004/0243141 A1 | 12/2004 | Brown et al. | |
| 2008/0058830 A1 | 3/2008 | Cole et al. | |
| 2008/0221585 A1 * | 9/2008 | Downer | A61F 2/1678 606/107 |
| 2008/0281333 A1 * | 11/2008 | Pessing | A61F 2/1678 606/107 |
| 2011/0015644 A1 | 1/2011 | Pankin et al. | |
| 2011/0046634 A1 * | 2/2011 | Rathert | A61F 2/1678 606/107 |
| 2012/0130390 A1 * | 5/2012 | Davies | A61F 2/1678 606/107 |
| 2018/0221142 A1 * | 8/2018 | Nguyen | A61F 2/1667 |

FOREIGN PATENT DOCUMENTS

| | | |
|---|---|---|
| WO | 1994007436 A1 | 4/1994 |
| WO | 2007027499 A2 | 3/2007 |
| WO | 2007078602 A2 | 7/2007 |
| WO | 2007080869 A1 | 7/2007 |
| WO | 2015070358 A2 | 5/2015 |

* cited by examiner

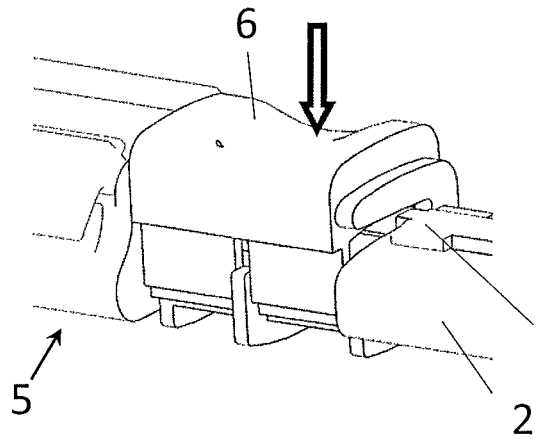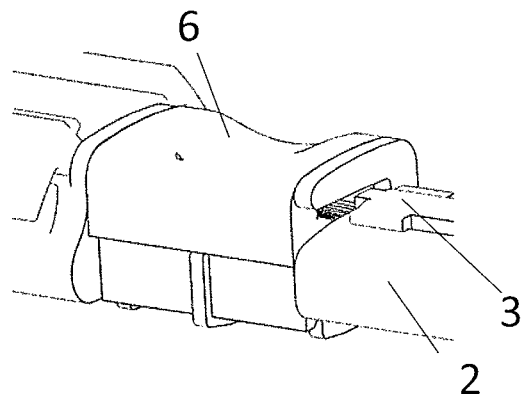
Fig. 5　　　　　　　Fig. 6
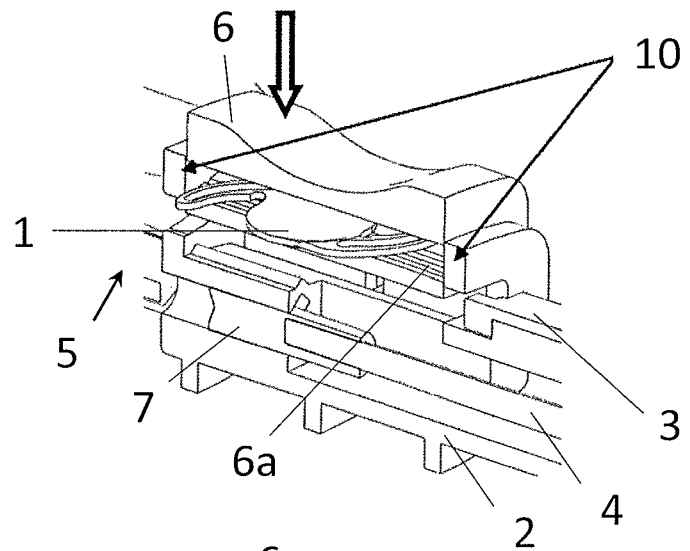
Fig. 7
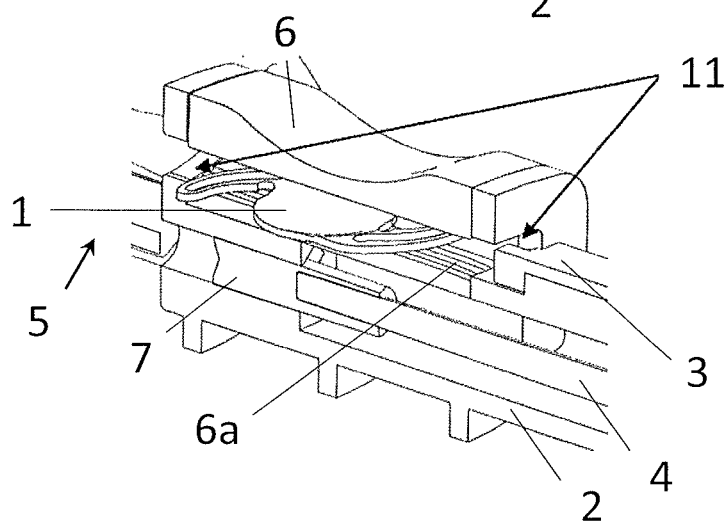
Fig. 8

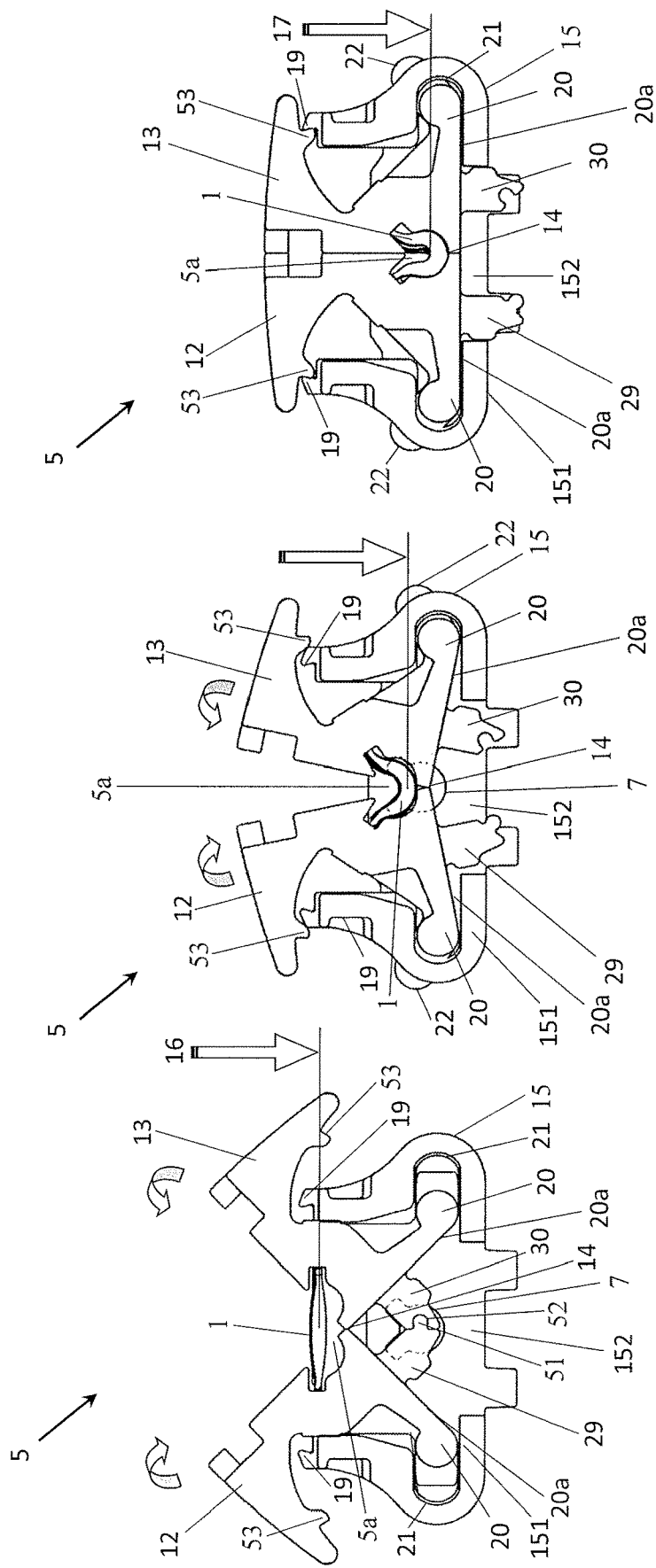

//<br>
FOLDING DEVICE AND INJECTOR SYSTEM FOR INTRAOCULAR LENSES

CROSS-REFERENCE TO RELATED APPLICATIONS

This application is a continuation-in-part of U.S. patent application Ser. No. 16/958,317, filed on Jun. 26, 2020, which in turn is a U.S. National Phase application under 35 U.S.C. 371 of PCT/HU2017/000053, filed Dec. 28, 2017, both incorporated herein by reference.

FIELD OF INVENTION

The present invention relates to a folding device for an intraocular lens and a surgical injector system comprising such a folding device.

BACKGROUND OF INVENTION

An IOL is an artificial lens implanted in the eye, for example, as a replacement for the natural crystalline lens after cataract surgery or to alter the optical properties of an eye in which the natural lens remains. IOLs include an optic, and preferably at least one flexible fixation member or haptic which extends from the optic and becomes affixed in the eye to secure the lens in position. The optic normally includes an optically clear lens. Implantation of such IOLs into the eye involves making an incision in the eye. It is advantageous, in order to reduce trauma and accelerate healing, to have an incision size as small as possible. Modern IOLs are foldable so that the IOL can be inserted through a smaller incision into the eye. A variety of instruments have been proposed to aid in inserting such a foldable lens in the eye.

In the beginning the surgeon simply used surgical forceps having opposing blades which were used to grasp the folded IOL and insert it through the incision into the eye. While this method is practically not in use anymore, most surgeons are using more or less sophisticated IOL injectors offering more control to the surgeon when inserting the IOL into the eye. IOL injectors have recently been developed with reduced diameter nozzles which allow for a much smaller incision to be made in the cornea than is possible using forceps only. Smaller incision sizes (e.g., less than about 3 mm) are preferred over larger incisions (e.g., about 3.2 to 5+mm) since smaller incisions have been attributed to reduced post-surgical healing time and complications such as induced astigmatism.

Since IOLs are very small and delicate articles of manufacture, great care must be taken in their handling. In order for the IOL to fit through the smaller incisions, they need to be folded and/or compressed prior to entering the eye wherein they will assume their original unfolded/uncompressed shape. The IOL injector device must therefore be designed in such a way as to permit the easy passage of the IOL through the device and into the eye, yet at the same time not damage the delicate IOL in any way. Should the IOL be damaged during delivery into the eye, the surgeon will most likely need to extract the damaged IOL from the eye and replace it with a new IOL, a highly undesirable surgical outcome.

Several types of injector systems are available today and can be clearly distinguished and separated regarding the loading of the IOL. There are mainly two types of non-preloaded injector systems: Most common are the winglet type cartridge injectors where the unfolded IOL has to be loaded from the side, being prefolded by the closing winglets and then pushed forward through the cartridge nozzle by a plunger with a tip made from a soft material. This generic type of non-preloaded injector is the most universal type, usable for many kinds of IOLs.

Disadvantage of injectors with non-preloaded winglet-type cartridge is the need to insert the IOL into the winglets by forceps requiring skill and experience of the user in order to avoid the risk of mishandling and/or damaging the lens during loading and closing the cartridge.

The other type of non-preloaded injector system has a fix-type cartridge that has to be loaded with the unfolded IOL from the back, where the lens is folded simply by being pushed through a narrowing cartridge nozzle by a pushing rod from hard material. These injector systems usually work only with hydrophobic IOLs and due to the lack of pre-folding of the IOL, the size of the nozzle tubes is larger. Patent specification WO1994007436 describes a non-preloaded winglet-type injector system with a pushing rod for hydrophobic IOLs Besides the non-preloaded injector systems there are different so-called preloaded injector systems. In case of some preloaded injector systems the hydrophobic IOL is placed into the injector during the assembly process of the injector and the IOL and the injector are packed, sterilized, stored and shipped together. These are the single-phase, truly preloaded IOL/injector systems.

Patent specifications U.S. Pat. No. 7,156,854 and WO2007080869 both describe such a single-phase, preloaded injector system with a hard pushing rod for hydrophobic IOLs.

In case of hydrophilic preloaded IOL/injector systems the IOL is usually preloaded in a special lens case or container, packed, sterilized, stored and shipped separately from the injector. Before injection the lens case/cartridge with the preloaded hydrophilic IOL has to be mounted on the injector, thus creating one injection system with a preloaded IOL. Some of these systems are winglet type, some of them backloaded type injectors.

Patent specification WO2007027499 describes an injector system for hydrophilic IOLs, enabling the user to load the IOL into the injector system without touching the IOL.

Patent specification WO2007078602 illustrates a folding arrangement for non-preloaded injectors in which small sized hydrophilic IOLs can be folded prior to injection by a rotational movement. However, the IOL is primarily stored in a vial before it has to be loaded into the cartridge.

Both arrangements are suitable for hydrophilic IOLs only and can be ruled out for hydrophobic IOLs.

Further types of injectors are disclosed in EP 2 286 762 A1; WO 2015/070358 A2; US 2011/015644 A1; US 2008/058830 A1; DE 10 2006 000929 A1.

Looking at these different kinds of injector systems, all of them with their own limitations, the objective of the present invention is to create a universal intraocular lens injector system that can be used as a preloaded or non-preloaded system, for hydrophobic or hydrophilic lenses. In all cases it is desired to use the same basic injector setup with the same type of folding device suitable for safely loading and injecting preloaded and non-preloaded IOLs, from hydrophobic or hydrophilic materials.

SUMMARY OF INVENTION

The inventors have realized that combining a winglet-type folding device with a controlled loading mechanism in a single device can result in an advantageous construction suitable for both non-preloaded and preloaded IOLs. This is accomplished by providing an injector body and a winglet type folding device removably positioned in the injector body. The folding device can be arranged such as to displace an IOL within the folding device from a level of a loading plane to a level of an injection plane while the IOL is being folded by the winglets.

In case of non-preloaded IOLs, i.e. when the injector and the IOL are shipped separately, this injector system is suitable for most types of foldable IOLs, both hydrophilic and hydrophobic. Its lens case allows a very simple and safe loading of the unfolded IOL minimizing the risk of any mishandling or damage of the IOL.

This injector system is also capable of receiving a closed lens case preloaded with an IOL, thus it is a 2-phase preloaded injection system for preloaded IOLs.

With the help of a modified lens case pre-assembled with the injector it can function as a single-phase preloaded IOL/injection system for hydrophobic IOLs.

In all cases the folding device provides two different levels (i.e. planes) for the IOL when the folding device is received in the injector. The loading of the IOL is carried out in the open position of the folding device at an upper plane, i.e. at the level of the loading plane. During closing of the folding device, two operations are performed at the same time: on one hand the IOL is pre-folded and on the other hand the pre-folded IOL descends from the upper loading level to a lower injection level, which is aligned with the axis of the injection plunger.

The injector system may further comprise a lens case, sitting behind the folding device, from where the loading of the IOL into the folding device can be carried out. This lens case has different embodiments. One embodiment that can be opened is mounted in a fixed position behind the folding device and has to be loaded with a non-preloaded IOL. Another embodiment of this lens case is preloaded, separately sterilized and packed with an IOL and can be mounted in a single step on the injector behind the folding device. A third embodiment of the lens case for preloaded hydrophobic IOLs is pre-mounted on the injector, having two positions: an upper storage/shipping position (i.e. level) and a lower loading position (i.e. level) where the lower loading level of the lens case is aligned with the upper loading level of the folding device mentioned above. Such a lens case is mounted on the injector in the upper (pre-loading) position providing safe storage/shipping function. During the usage, the lens case is lowered to the loading position, to the loading level. This embodiment of the lens case in cofunction with the folding device creates three different functional levels (i.e. planes) for the IOL in the injector: a storage/shipping level, a loading level and an injection level.

Accordingly, the invention relates to an injector system for injecting foldable IOLs. The injector system comprises a folding device with a nozzle tube, a lens case, an injector body, an injection plunger. The injector body accommodates the injection plunger the axis of which lies at a level of an injection plane. The folding device comprises two winglets connected to each other by a hinge joint providing an open and a close position for the folding device. In the open position of the folding device, the inner surface of the winglets forms a loading channel on a level of a loading plane. In the closed position of the folding device, the inner surface of the winglets forms an injection channel on the lower level of the injection axis, where the axis of the injection channel coincides with the axis of the injection plunger.

Optionally, a lens case is attached to the injector body behind the folding device. The inner surface of the lens case forms an inner space for the unfolded IOL.

In an advantageous embodiment, the lens case attached to the injector body has a pre-loading position where the plane of the inner space of the lens case is above the level of loading, and a loading position where the plane of the inner space of the lens case is on the level of the loading plane, where the longitudinal axis of the inner space coincides with the axis of the loading pusher. In other words, three levels are defined for the IOL in this embodiment: 1.) storage and shipping the IOL in the pre-loading position of the lens case, 2.) loading of the IOL in the loading position of the lens case that is on the level of the loading plane and 3.) the level of the injection axis.

This construction allows the IOL to be loaded, folded and injected by the injector in a safe way preventing mishandling and damage of the IOL.

BRIEF DESCRIPTION OF DRAWINGS

For a more complete understanding of the invention, reference is made to the following detailed and the accompanying drawings wherein:

FIGS. 5 and 6 show the lens case for hydrophobic preloaded IOL in the injector by side view;

FIGS. 7 and 8 show the lens case for hydrophobic preloaded IOL in the injector by a sectional view;

FIGS. 36A, 36B and 36C schematically illustrate the structure and operation of the folding device arranged in the receiver of the injector body according to FIGS. 26 and 28.

DESCRIPTION OF PREFERRED EMBODIMENTS

In the following, for purpose of explanation and not limitation, specific details of an injector for IOLs are set forth, in order to provide a thorough understanding of the present invention. It will be apparent to one skilled in the art that the present invention may be practiced in other embodiments that depart from these specific details.

First Embodiment of an Injector System for Non-Preloaded IOL

Figure 1:
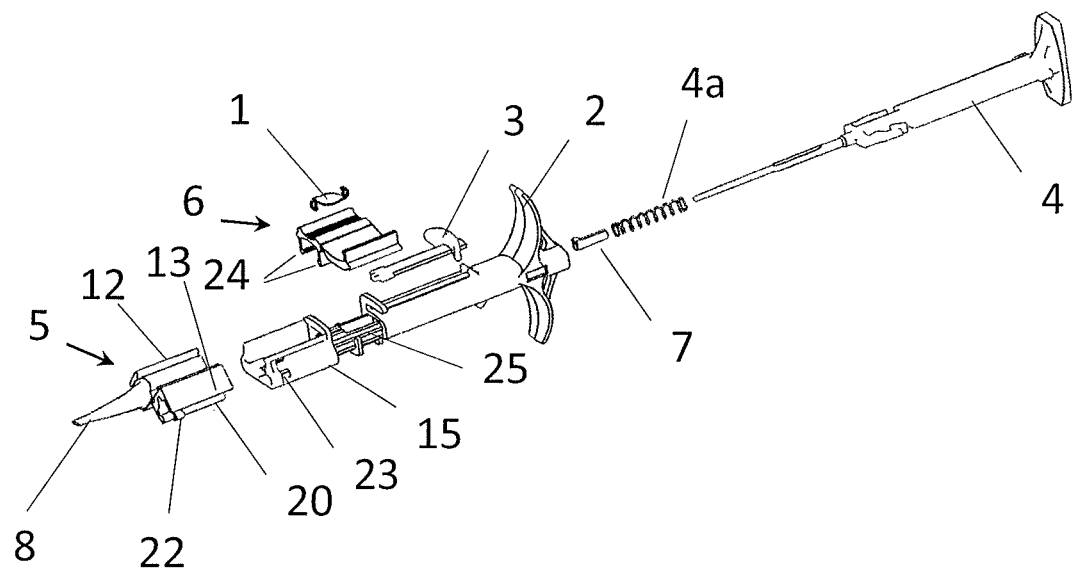
FIG. 1 shows a first embodiment of the injector according to the invention for a non-preloaded IOL in disassembled state.

FIG. 1 shows the parts of an injector system for injecting non-preloaded IOL 1. The IOL 1 can be any conventional deformable intra-ocular lens that is suitable for injecting into an eye of a patient. Accordingly, the IOL 1 depicted in the FIGS. is only illustrative and is not intended to limit the application of the injector system according to the invention.

In this embodiment the injector system comprises a folding device 5 with a nozzle tube 8, a lens case 6, an injector body 2, an injection plunger 4 and a loading pusher 3. At the end of the injection plunger 4 a soft tip 7 is arranged. The injector body 2 removably holds folding device 5 and accommodates the loading pusher 3 as well as the injection plunger 4. The axis of the two plungers are parallel to each other and both are accommodated in the injector body 2 in which they can reciprocate. The loading pusher 3 moves above the injection plunger 4 in a different plane. The injector body 2 is provided with a receiver 15 for receiving the folding device 5 therein. The folding device 5 has two co-acting winglets 12, 13 connected to one another and pivotable with respect to one another as will be explained in more detail in connection with FIGS. 9A-9C. The nozzle tube 8 is preferably carried by one of the winglets 12, 13, in the present case to the winglet designated with reference numeral 12. The nozzle tube 8 may be formed unitary with winglet 12 or it may be attached to it by any suitable means, e.g. adhesive, snap-fit connection, etc. A leg portion 20 of at least one winglet 13 is provided with a protrusion 22 fitting to a cavity 23 in the receiver 15 of the injector body 2 when the folding device 5 is in its closed position. The protrusion 22 fitting to a cavity 23 in the receiver 15 of the folding device 5 in its closed position ensures that the folding device 5 cannot be removed inadvertently from the injector body 2 after closing the folding device 5. In this embodiment, the bottom of the lens case 6 is provided with rims 24 and the injector body 2 is provided with grooves 25. The lens case 6 is attached to the injector body 2 behind the folding device 5. The lens case 6 has a supporting surface 6a on which the unfolded IOL 1 is placed (see FIG. 12). The lens case 6 is provided with a hinged lid 9 the inner surface of which defines an inner space of the lens case 6 together with the supporting surface 6a. The IOL 1 is not part of the injector system, it can be placed into the lens case 6 of the injector body 2 just before the usage.

Figure 2:
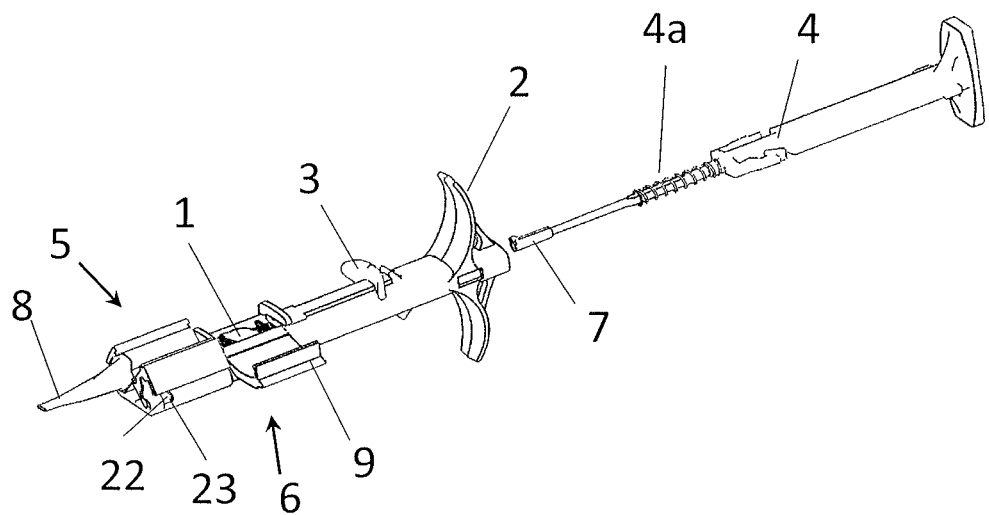
FIG. 2 shows the injector according to FIG. 1 in assembled state.

FIG. 2 shows the assembled injector system for the non-preloaded IOL 1. All parts, i.e. the injector body 2, the folding device 5 with the nozzle tube 8, the lens case 6 and the loading pusher 3 are put together except the injection plunger 4 with the soft tip 7. The IOL 1 is inserted in the lens case 6. The lens case 6 is connected to the injector body 2 by the rims 24 and the grooves 25 depicted in FIG. 1. In this assembled state a longitudinal axis of the inner space of the lens case 6 coincides with an axis of the loading pusher 3 when the rims 24 of the lens case 6 fit to the grooves 25 of the injector body 2. The lens case 6 is provided with a lid 9 hinging on the lens case 6, by which the lens case 6 can be closed after the IOL 1 was inserted in the inner space of the lens case 6. The protrusion 22 on the leg portion 20 of the winglet 13 fits to a cavity 23 in the receiver 15 of the folding device 5. In further embodiments, more than one protrusion 22 can be provided on the leg portion 20 of the winglet 13 or further protrusions can be provided on the flange of the other winglet 12 too.

Second Embodiment of an Injector System for Hydrophobic Preloaded IOLs

Figure 3:
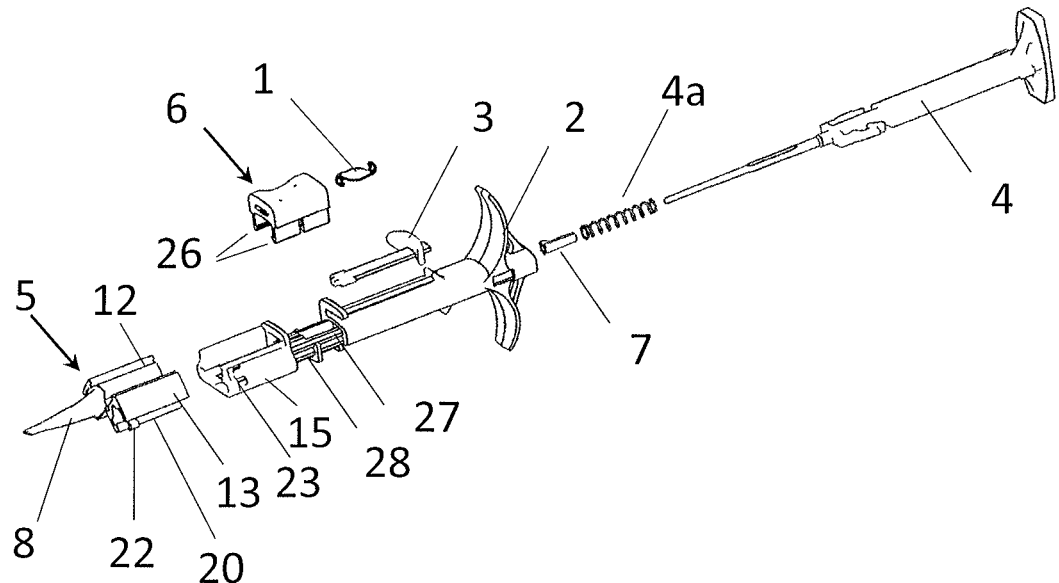
FIG. 3 shows a second embodiment of the injector according to the invention for a hydrophobic preloaded IOL in disassembled state.

FIG. 3 shows the parts of another preferred injector system for injecting hydrophobic preloaded IOL 1. In this embodiment the injector system also comprises a folding device 5 with a nozzle tube 8, a lens case 6, an injector body 2, an injection plunger 4 and a loading pusher 3. At the end of the injection plunger 4 a soft tip 7 is arranged. The injector body 2 accommodates the loading pusher 3 and the injection plunger 4 similar to the embodiment in FIGS. 1 and 2. The axes of the two plungers are also parallel to each other and both are accommodated in the injector body 2 in which they can reciprocate. The loading pusher 3 moves above the injection plunger 4 in a different plane. The structure of the folding device 5 with the two winglets 12, 13, the leg portion 20, the protrusion 22 fitting to a cavity 23 in the receiver 15 of the folding device 5 in its closed position can be configured identically as described in case of the previous embodiment. The receiver 15 of the folding device 5 is also part of the injector body 2. The lens case 6 is attached to the injector body 2 behind the folding device 5, the inner surface of the lens case 6 forms an inner space for the unfolded IOL 1. The difference to the injector system of non-pre-loaded IOL is that the bottom of the lens case 6 is provided with rims 26 fitting to upper grooves 27 of the injector body 2 in a pre-loading position of the lens case 6 and fitting to lower grooves 28 in a loading position of the lens case 6 below the pre-loading position. So the lens case 6 can be attached to the injector body 2 in two positions. In the pre-loading position, where the longitudinal axis of the inner space of the lens case 6 is above the level of the loading plane and the IOL 1 cannot be loaded to the folding device 5, and in the loading position where the longitudinal axis of the inner space of the lens case 6 is on the level of the loading plane 16, where the longitudinal axis of the inner space coincides with the axis of the loading pusher 3. In this embodiment, the IOL 1 is part of the injector system, they are packed and shipped together.

Figure 4:
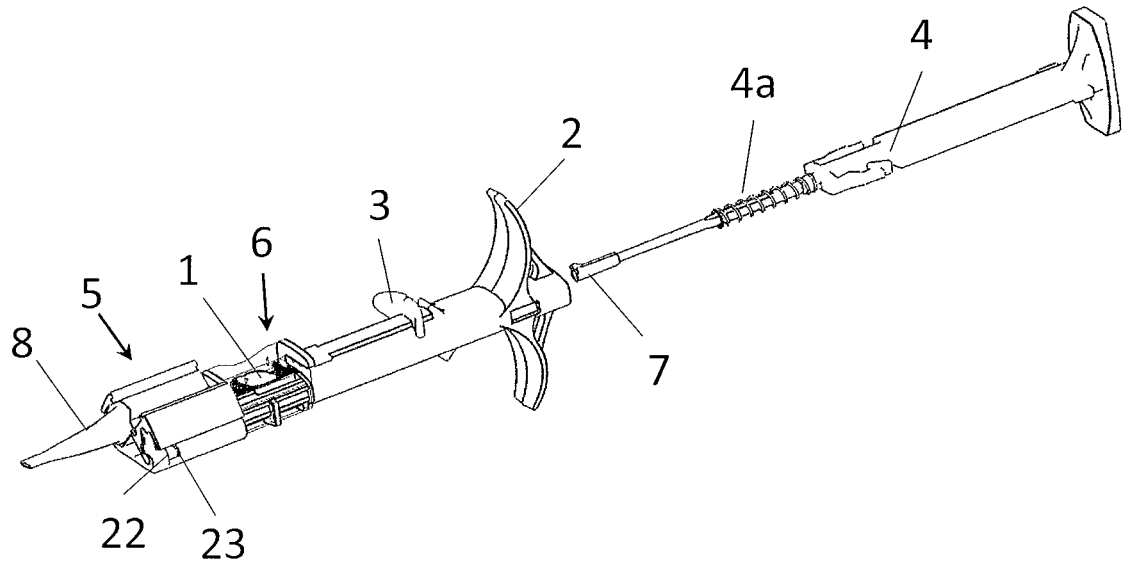
FIG. 4 shows the injector according to FIG. 3 in assembled state.

FIG. 4 shows the assembled injector system for preloaded IOL 1. All parts, i.e. the injector body 2, the folding device 5 with the nozzle tube 8, the lens case 6 and the loading pusher 3 are put together except the injection plunger 4 with the soft tip 7. The protrusion 22 on the leg portion 20 of the winglet 13 fits to a cavity 23 in the receiver 15 of the folding device 5 like in the non-preloaded case. The injector body 6 is shown transparently in this figure to reveal the position of the IOL 1 in the inner space of the lens case 6.

FIGS. 5, 6, 7 and 8 show the detailed structure and position of the lens case 6 comprising the IOL 1 with respect to other parts of the injector system. FIGS. 5 and 6 show the step of preparation for loading the preloaded IOL 1. As it was mentioned, preloaded IOL 1 is shipped in the lens case 6 as part of the injector system. The lens case 6 is attached to the injector body 2 behind the folding device 5 in a pre-loading position as it is illustrated in FIG. 5. Then the lens case 6 is pushed down to a lower loading position, in the direction of the arrow. The loading position can be seen in FIG. 6. Separation of the upper pre-loading position and the lower loading position can prevent inadvertent loading of the IOL 1.

In order to keep the IOL 1 in the lens case 6 during storage and shipment but let it be loaded into the folding device 5 before the usage, two gates 10 are provided on the injector body 2 at both ends of the lens case 6 closing both end of the inner space of the lens case 6 in its pre-loading position as it is shown in FIG. 7. In the pre-loading position of the lens case 6, gates 10 prevent the IOL 1 getting out of the lens case 6. FIG. 7 is a sectional view that also illustrates the end of the loading pusher 3 and the end of the injection plunger 4 with the soft tip 7 reciprocating in different planes.

When the lens case 6 is moved to the loading position, as it is depicted in the sectional view of FIG. 8, openings 11 provided in the gates 10 at both ends of the lens case 6 allow the loading pusher 3 to move the IOL 1 across the lens case 6 to the folding device 5.

Figure 24:
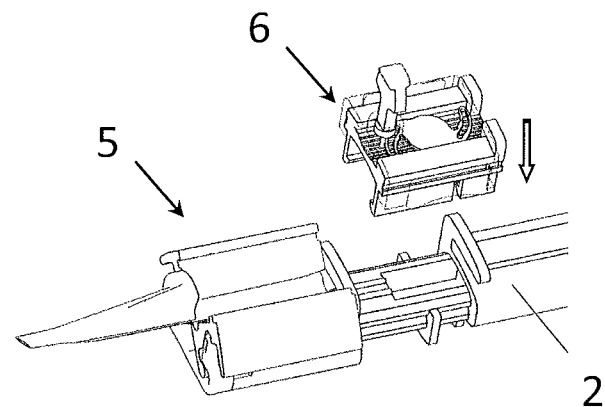
FIG. 24 shows the docking step of the IOL preloaded in a separate lens case.

Third Embodiment of an Injector System for Hydrophilic or Hydrophobic IOLs Preloaded in a Separate Lens Case FIG. 24 shows an embodiment of the injection system with a lens case 6 for hydrophilic or hydrophobic preloaded IOL 1. The structure of this system is similar to the one described for hydrophobic preloaded IOL 1 in connection with FIGS. 3 and 4, however, the lens case 6 is different. In this embodiment the lens case 6 has a lower portion capable for docking to the injector body 2. The arrow indicates the direction of the docking. After docking, the lens case 6 takes up a position for loading the IOL 1, i.e. the level of the plane where the IOL 1 is situated inside the lens case 6 coincides with the level of the loading plane where the IOL 1 can be pushed into the folding device 5.

In FIG. 25, the lens case 6 is attached to the injector body 2. The lens case 6 comprises a stopper 34 that has to be removed before loading the IOL 1 into the folding device 5. Direction of removal of the stopper 34 is show by the arrow.

FIG. 25 shows that the lens case 6 comprises a hole 33. Through the hole 33 visco-elastic material can be injected into the lens case 6 to minimize the friction between the IOL 1 and the inner spaces of the injector system during loading and injecting the IOL 1.

Figures 9A, 9B, 9C:
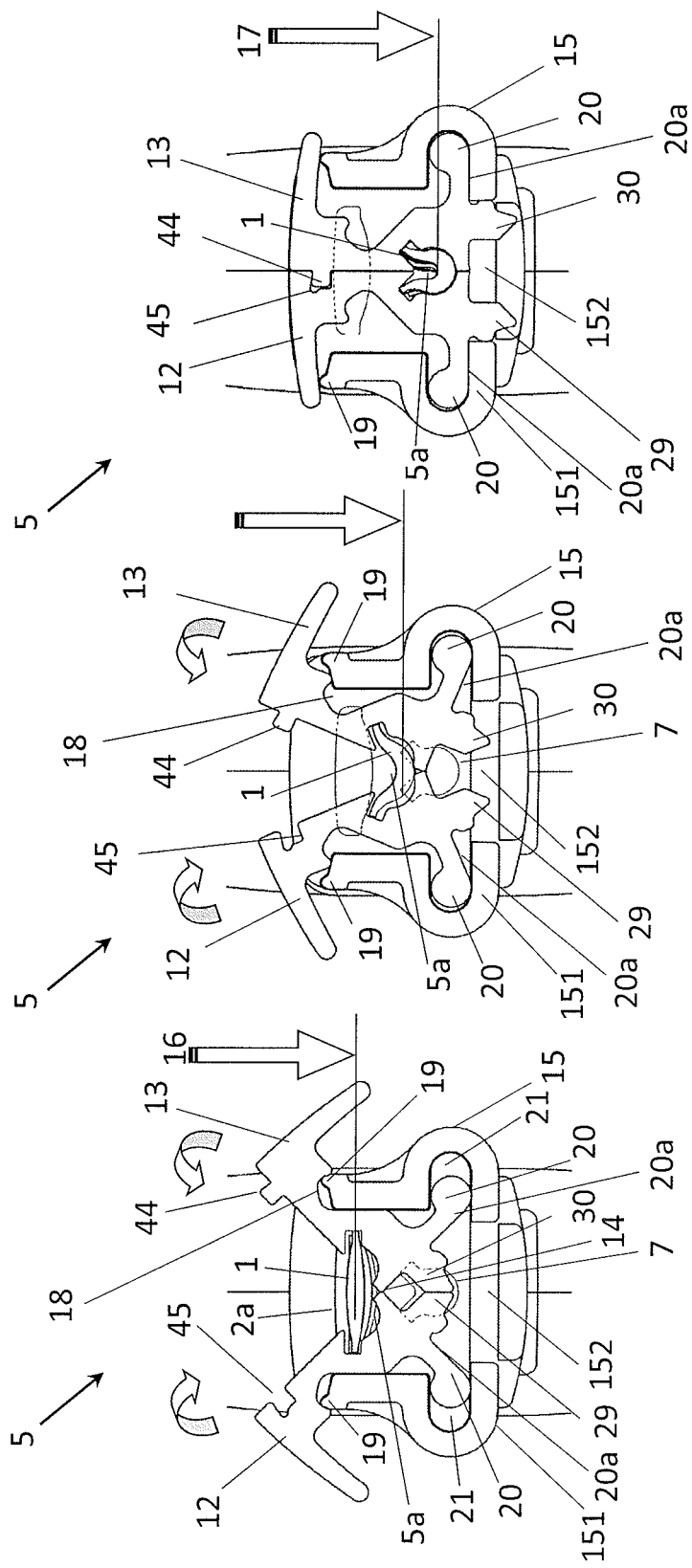
FIGS. 9A, 9B and 9C schematically illustrate the structure and operation of a folding device arranged in a receiver of an injector body.

The Folding Device of the Injector System According to the First Three Embodiments FIGS. 9A, 9B and 9C illustrate the structure and operation of the folding device 5 used in the above discussed injector systems. The folding device 5 is removably positioned in receiver 15 of injector body 2 and comprises two co-acting winglets 12, 13 connected to each other by a hinge joint 14 defining a hinge axis. The winglets 12, 13 are pivotable about the hinge axis between an open position and a closed position of the folding device 5 along the hinge joint 14. Winglets 12, 13 together define receptacle 5a for an IOL and an open channel which serves as a loading channel or an injection channel for the IOL depending on winglet position. The open position for winglets 12, 13 is illustrated in FIG. 9A, the closed position in FIG. 9C. FIG. 9B shows an intermediate phase between the open position and the closed position. In the open position of the folding device 5, the inner surfaces of the winglets 12, 13 together define receptacle 5a, which also serves as a loading channel for the IOL 1 at the level of a loading plane 16, where the loading plane 16 is defined such that the axis of the loading pusher 3 lies in the loading plane 16. In the closed position of the folding device 5 the receptacle 5a formed by the inner surface of the winglets 12, 13 has an altered shape and serves as an injection channel for the IOL 1 at the level of an injection plane 17. The injection plane 17 is defined such that the axis of the injection plunger 4 lies in the injection plane 17. The loading plane 16 as well as the injection plane 17 extend in a direction that is perpendicular to the cross-section illustrated in FIGS. 9A-9C.

The cross-section of the soft tip 7 of the injection plunger 4 corresponds to the cross-section of the receptacle 6a when it serves as an injection channel at its entry, i.e. on its side opposite of the nozzle 8, whereby the tip 7 fills out the receptacle 5a when the injection plunger 4 is pushed forward (in the distal direction) and the soft tip 7 enters the receptacle in order to prevent jamming of the IOL 1 as it is pushed forward. The position of the soft tip 7 of the injection plunger 4 is illustrated by dotted line in FIGS. 9A and 9B. The cross-section of the receptacle may be narrowing in the direction of the nozzle 8 in order to render the IOL 1 even more compact before it enters the nozzle 8 through its inlet opening adjacent the folding device 5 (not shown). The shape of the cross-section of the receptacle 5a in the closed position of the folding device 5 may also change along its longitudinal axis, for example the cross-section may become gradually more circular (starting from the irregular shape depicted in FIG. 9C) in the direction of the nozzle 8. The cross-section of the nozzle inlet opening corresponds to the cross-section of the receptacle 5a in the closed position of the folding device 5 on its exit side (adjacent the nozzle 8) in such a way that the cross-section of the nozzle inlet opening is the same or slightly greater in order to permit unhindered passage of the IOL 1 from the receptacle into the nozzle 8.

The outer surface of the winglets 12, 13 at their upper parts are provided with recesses 18 fitting to flanges 19 of the receiver 15 of the folding device 5 in the open position of the folding device 5. The winglets 12, 13 are further provided with leg portions 20 at their bottom parts fitting into recesses 21 of the receiver 15 of the injector body 2 when the folding device and the winglets are in the closed position. The leg portions 20 each define a base plane 20a that includes the hinge axis. The two base planes 20a are at an angle, preferably at right angle relative to one another when the winglets 12, 13 are in the open position and the two base planes 20a merge into a single plane when the winglets 12, 13 are in the closed position.

The folding device 5 is removably held in the receiver 15 of the injector body 2. The receiver 15 has a base portion 151 provided with a base opening 152. The leg portion 20 of each winglet 12, 13 is supported and guided by the base portion 151 of the receiver 15 as the winglets 12, 13 are pivoted from the open to the closed position whereby the leg portions 20 slide away from each other within the two side recesses 21 of the receiver 15. When the winglets 12, 13 are completely closed the base planes 20a merge into a single plane which comes in contact with the internal side of the base portion 151 of the receiver 15. In this position the protuberances 29, 30 of each leg portion 20 extend through the base opening 152 of the receiver 15 as can be seen in FIG. 9C.

This arrangement results in a lowering of the IOL 1 from the level of the loading plane 16 to the level of the injection plane 17. In FIG. 9A, the winglets 12, 13 are in the open position. The IOL 1 is loaded into the folding device 5 by the loading pusher 3 arranged at the level of loading plane 16. An opening 2a is formed on the injector body 2 behind the two winglets 12, 13 so as to connect the inner space of the lens case 6 and the receptacle 5a of the folding device 5 in the open position of the winglets 12, 13, which opening 2a is illustrated in FIGS. 9A-9C partly by dotted line. The opening 2a is dimensioned so as to allow the loading pusher 3 to pass through in order to push the IOL into the receptacle 5a when it is at the level of the loading plane 16 in the open position of the folding device 5. Then the folding device 5 is closed by pivoting the winglets 12, 13 in the direction of each other as it is indicated by the arrows in FIGS. 9A and 9B. In FIG. 9C, the folding device 5 is closed and thereby the IOL 1 is displaced to the level of the injection plane 17 by the winglets 12, 13. The lowering of receptacle 5a by operation of the winglets 12, 13 is based on the interaction of the flanges 19 of the receiver 15 of the folding device 5 with the recesses 18 of the winglets 12, 13, as well as on the interaction of the leg portions 20 of the winglets 12, 13 at their bottom part with the recesses 21 of the receiver 15 of the injector body 2. During the closing process the recesses 21 of the receiver 15 cause the winglets 12, 13 not just to pivot but to move downwards too. With this downward movement the receptacle 5a of the folding device 5 with the IOL 1 is displaced from the level of the loading plane 16 to the level of the injection plane 17 its shape changing gradually as the position of two winglets 12, 13 change and it is eventually transformed into the injection channel. During the closing process, the IOL 1 is distorted from an unfolded shape (IOL 1 in FIG. 9A) to a folded shape (IOL 1 in FIG. 9C) and the injection channel form of the receptacle 5a is configured to keep the IOL 1 in the folded state. The folded shape is necessary for safe injection through the nozzle tube 8 into a patient's eye.

In order to keep the folding device 5 securely in the closed position, the inner surface of one of the winglets 13 at its upper part can be provided with a rim 44 fitting to a groove 45 of the other winglet 12 at their upper part.

In and advantageous embodiment, the leg portions 20 are provided with motion limiting protuberances 29, 30 extending from the base planes 20a. The protuberances 29, 30 abut one another when the winglets 12, 13 are in the open position (FIG. 9A) blocking a path of the injection plunger 4. The protuberances 29, 30 coming in contact with each other in the open position of the folding device 5 prevent inadvertent injection by blocking the injection plunger 4 from moving forward into the folding device 5 as well as act as limiters for the winglets 12, 13 in the open position.

Operating the Injector Systems According to the First Three Embodiments

In the next figures, the operating steps for non-preloaded and preloaded IOLs of FIGS. 1-2 and FIGS. 3-4 are described simultaneously in order to highlight the difference between the two methods.

Figure 10:
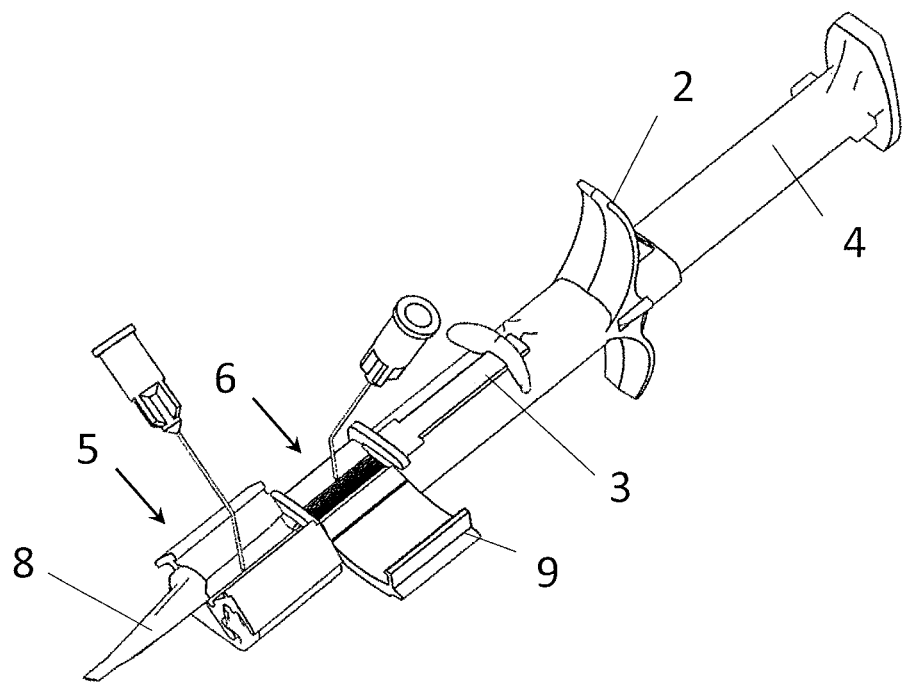
FIG. 10 shows the step of injecting visco-elastic material to the folding device and to the lens case of the non-preloaded IOL.

FIG. 10 shows the first step of operating an injector for injecting non-preloaded IOL comprising a folding device 5 with a nozzle tube 8, a lens case 6, an injector body 2, an injection plunger 4 and a loading pusher 3. In this step, visco-elastic material is injected into the open folding device 5 and into the open lens case 6. Visco-elastic material reduces the friction between the IOL 1 and the inner surface of the folding device 5 and the lens case 6.

Figure 11:
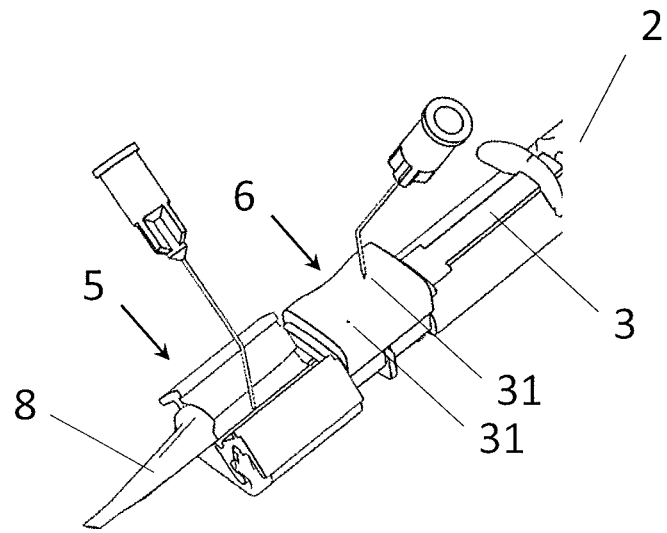
FIG. 11 shows the step of injecting visco-elastic material to the folding device and to the lens case of the hydrophobic preloaded IOL.

FIG. 11 shows the same step with an injector for injecting hydrophobic preloaded IOL. In this figure a part of the injector body 2 is illustrated only focusing on the difference with respect to the previous case. In this case, the visco-elastic material is injected through holes 31 prepared on the top of the lens case 6, which has been attached to the folding device 5.

Figure 12:
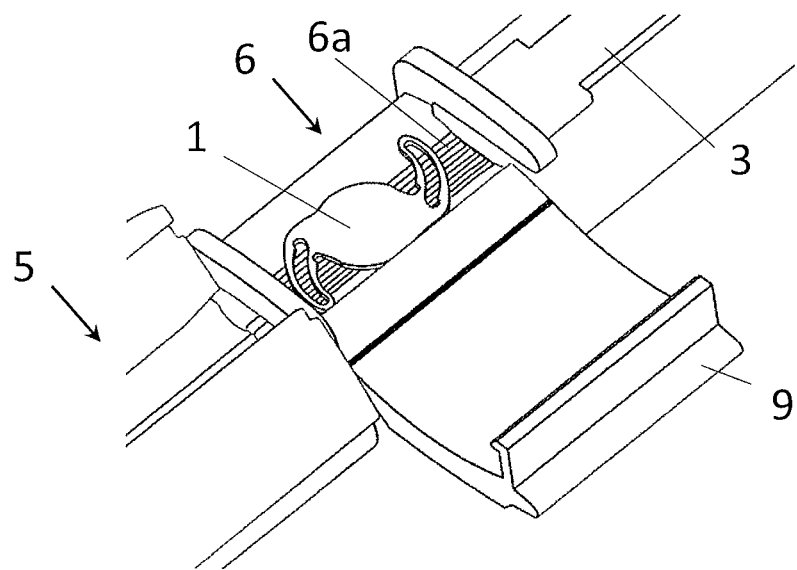
FIG. 12 shows the step of placing the non-preloaded IOL in the lens case.

In FIG. 12, the non-preloaded IOL 1 is placed into the lens case 6 having a lid 9 hinging on the lens case 6. Placing the IOL 1 into the lens case 6 requires no special exercise, since there is no need of pre-folding the IOL 1 at this stage. This step is missing in case of a hydrophobic preloaded IOL 1.

Figure 13:
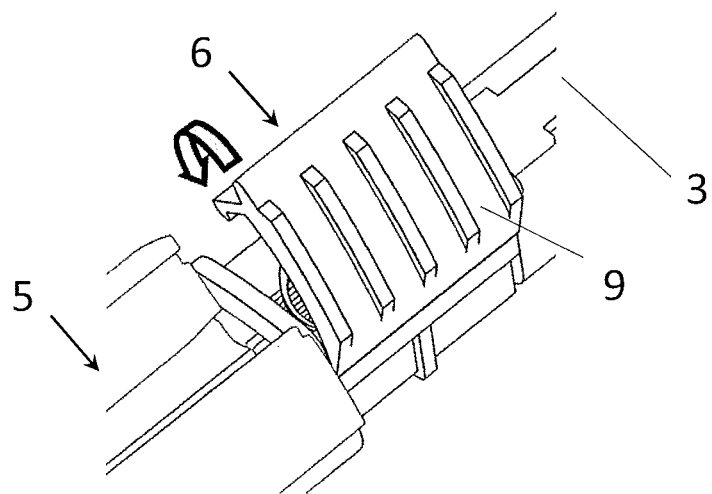
FIG. 13 illustrates the closing step of the lens case for non-preloaded IOL.

FIG. 13 illustrates the closing step of the lens case 6 for non-preloaded IOL 1.

The lid 9 is closed on the body of the lens case 6 as depicted by the arrow. By this step the IOL 1 is ready for loading.

Figure 14:
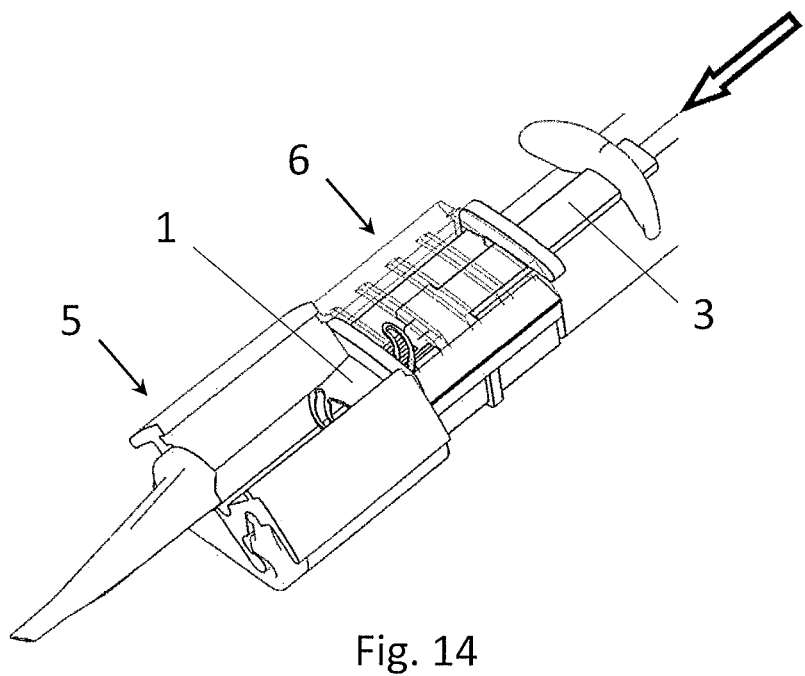
FIG. 14 shows the loading step when the non-preloaded IOL is moved to the folding device.

FIG. 14 shows the next step when the non-preloaded IOL 1, placed in the lens case 6, is moved to the folding device 5 by pushing forward the loading pusher 3 as it is indicated by the arrow.

Figure 15:
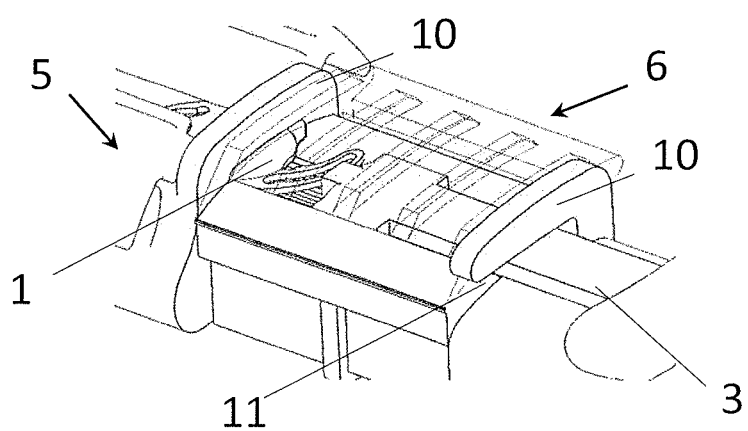
FIG. 15 shows the same loading step from another view.

FIG. 15 shows the same step from another view. The loading pusher 3 is moving through the openings 11 below the gates 10 to the folding device 5 pushing the IOL 1 from the lens case 6 to the folding device 5.

Figure 16:
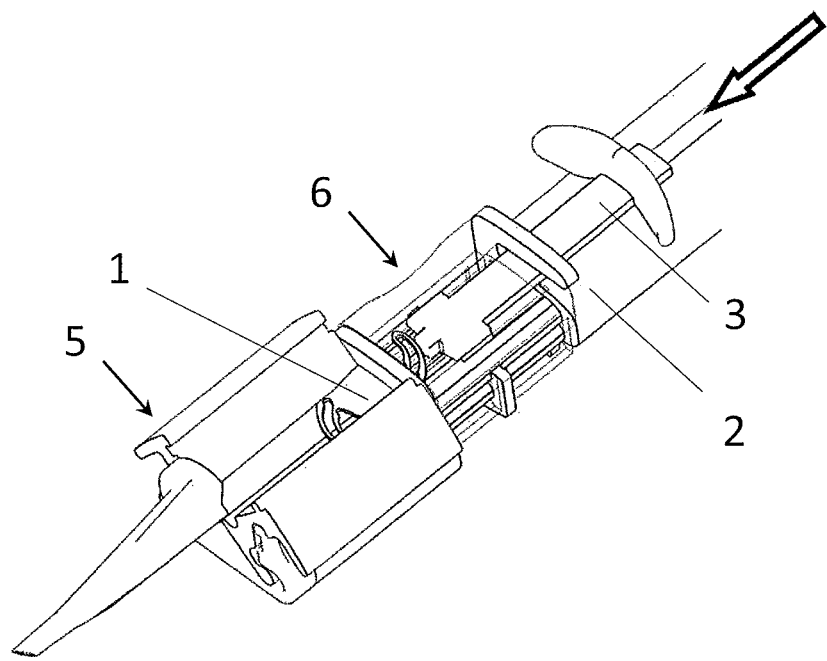
FIGS. 16 and 17 show the loading step for hydrophobic preloaded IOL.
Figure 17:
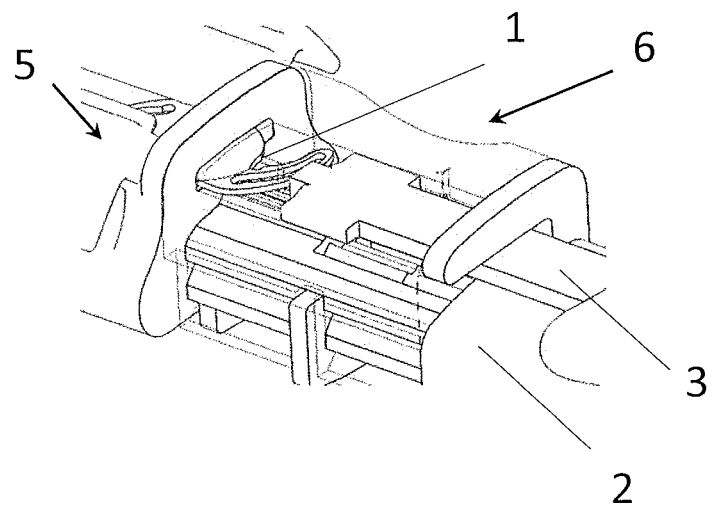

The same operation is carried out for the hydrophobic preloaded IOL 1 according to FIG. 16 and FIG. 17. In this phase, the IOL 1 is leaving the lens case 6 and entering the receptacle 5a of the folding device 5 moved by the loading pusher 3.

Figure 18:
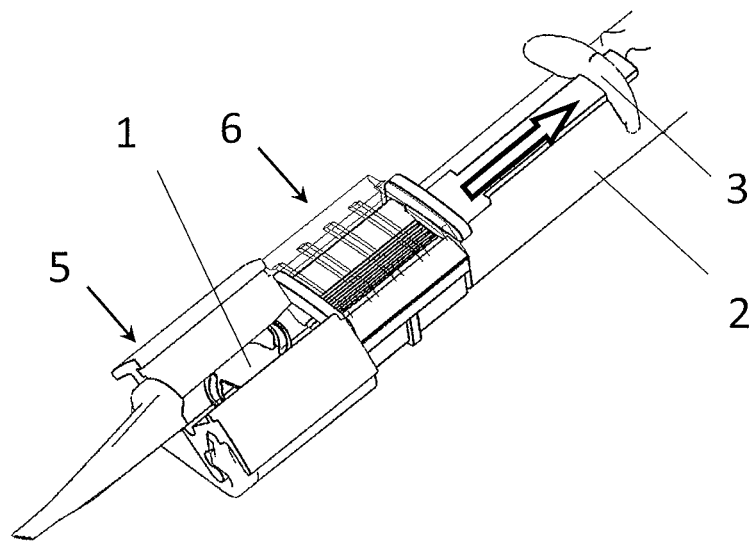
FIG. 18 and FIG. 19 show the step of pulling back the loading pusher for non-preloaded and for hydrophobic preloaded IOL, respectively.
Figure 19:
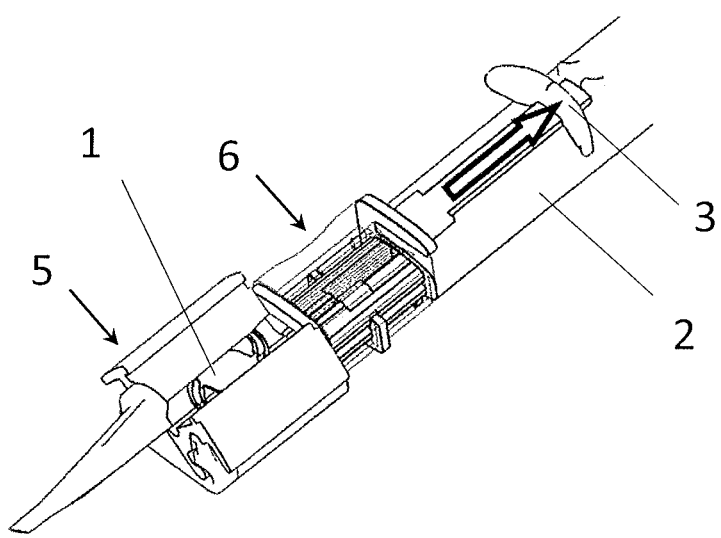

After the loading step, the loading pusher 3 is pulled back in case of non-preloaded as well as in case of preloaded IOL as it is shown in FIG. 18 and FIG. 19, respectively. Lens cases 6 are depicted transparently, to show that their inner space is empty.

Figure 20:
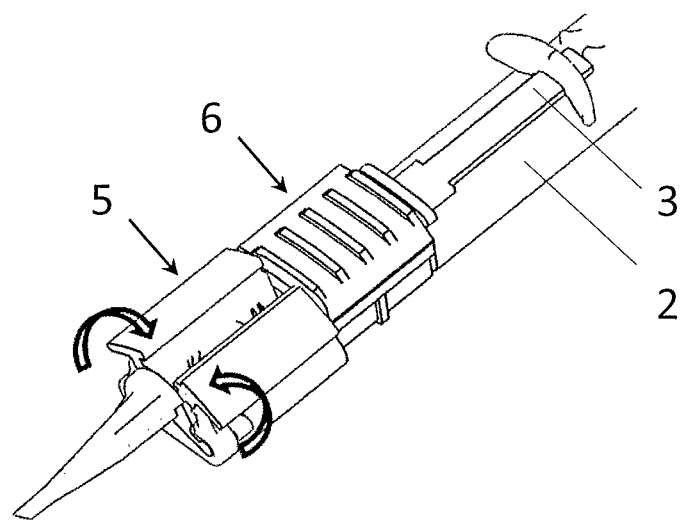
FIG. 20 shows the closing step of the folding device for non-preloaded IOL.
Figure 21:
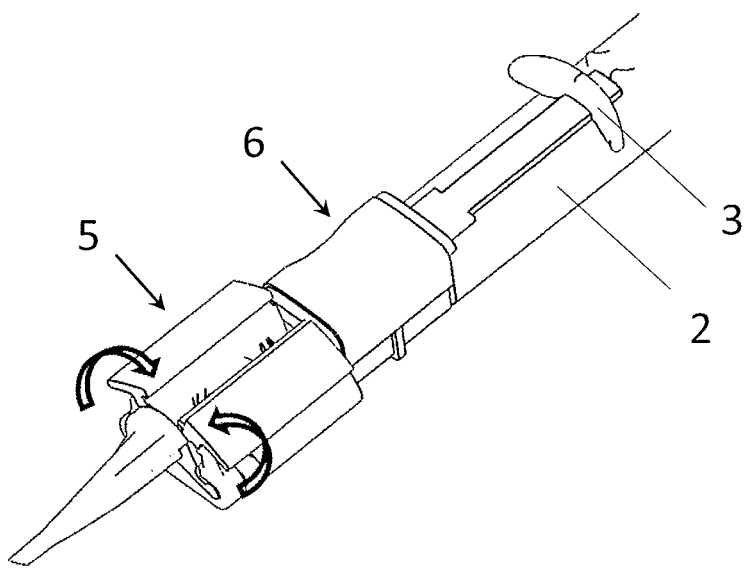
FIG. 21 shows the closing step of the folding device for hydrophobic preloaded IOL.

FIG. 20 shows the closing step of the folding device 5 for non-preloaded IOL 1 and FIG. 21 for the hydrophobic preloaded IOL 1 whereby the IOL 1 is lowered from the loading level to the injection level as described in detail in connection with FIGS. 9A-9C. The closing of the folding device 5 is indicated by arrows.

Figure 22:
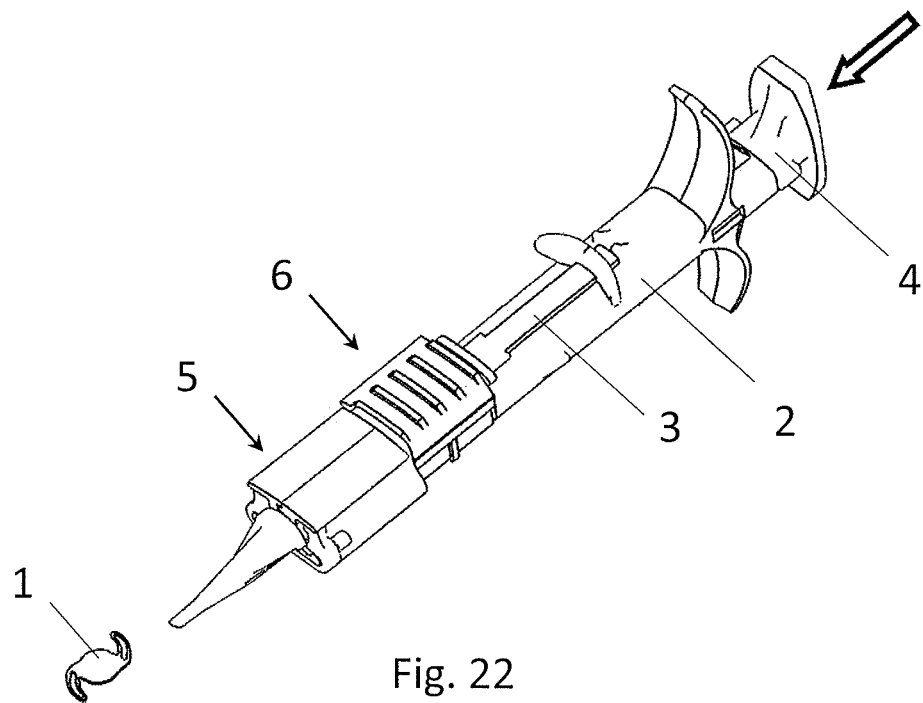
FIG. 22 shows the injection step for non-preloaded IOL.
Figure 23:
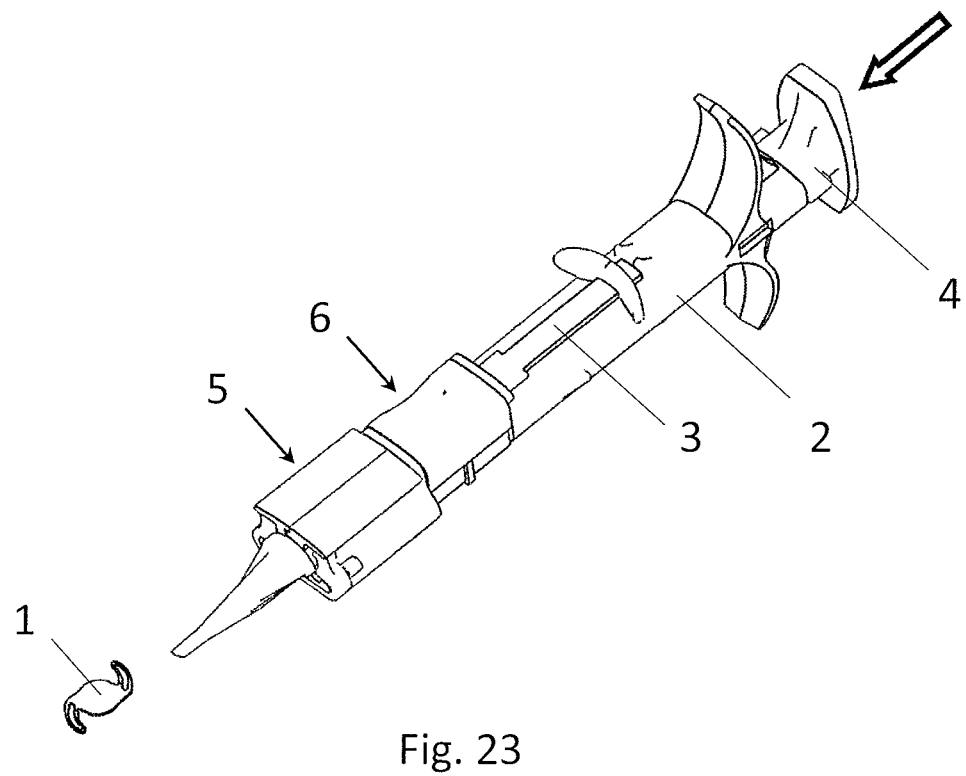
FIG. 23 shows the injection step for hydrophobic preloaded IOL.

When the folding device 5 is in the closed position and the IOL 1 in the receptacle 5a of the folding device 5 has reached the level of the injection plane 17, the injection plunger 4 is pushed forward, thereby injecting the IOL 1 into the patient's eye. This step is also identical both for non-preloaded IOL as shown in FIG. 22, and for hydrophobic preloaded IOL 1 shown in FIG. 23.

In case of injecting a hydrophilic or hydrophobic IOL preloaded in a separate lens case 1 such as the lens case 6 illustrated in FIG. 24, the method comprises the steps of a.) mounting the lens case 6 preloaded with a hydrophilic or hydrophobic IOL 1; b.) injecting visco-elastic material into the open folding device 5 and into the lens case 6 through a hole 33; c.) moving the IOL 1 into the folding device 5 by pushing forward the loading pusher 3; d.) pulling back the loading pusher 3; e.) closing the folding device 5; f.) injecting the IOL 1 by pushing forward the injection plunger 4.

Figure 25A:
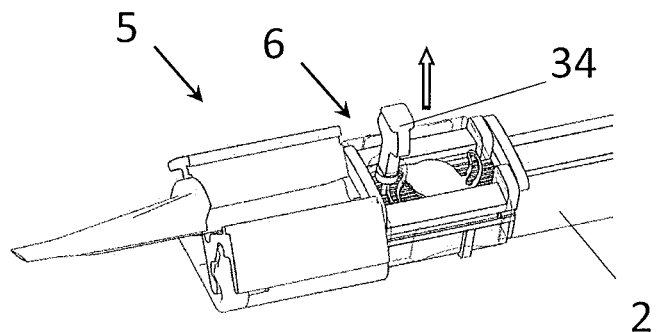
FIG. 25a shows the removal step of the stopper from the lens case for preloaded IOL.
Figure 25B:
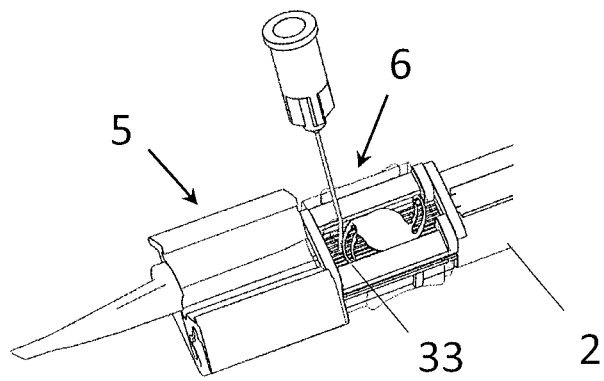
FIG. 25b shows injection step of visco-elastic material into the lens case for a preloaded IOL

FIGS. 24, 25a, 25b show the steps that are different from the operating steps of the hydrophobic preloaded IOL 1. FIG. 24 shows the docking step of the lens case, FIG. 25a shows the removal step of the stopper 34 from the lens case 6 and FIG. 25b shows the step of injecting visco-elastic material into the lens case 6 through the hole 33 that accommodated the stopper 34.

Figure 26:
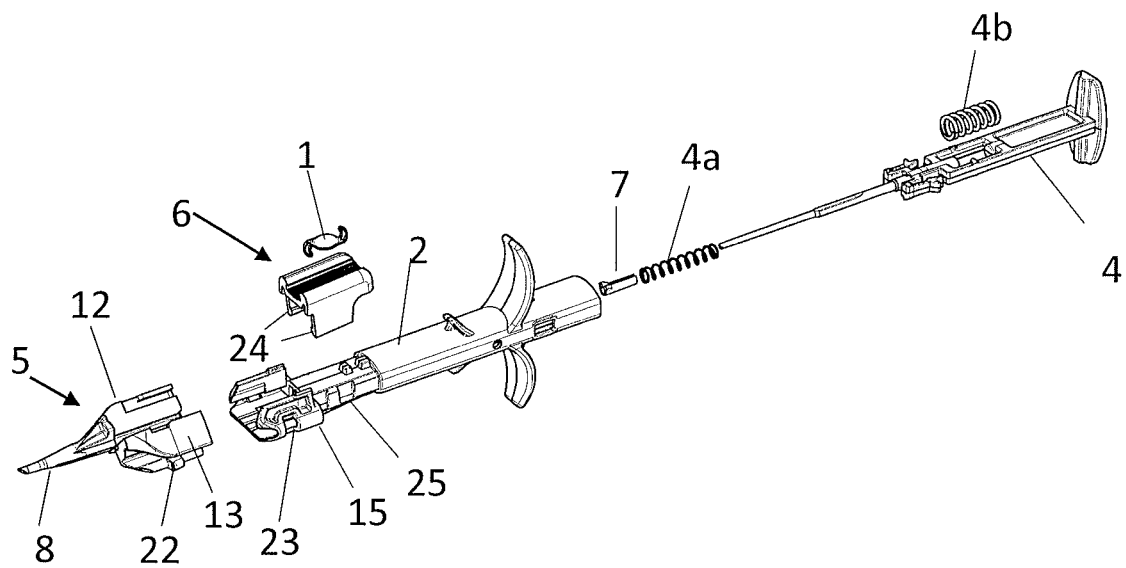
FIG. 26 shows a third embodiment of the injector according to the invention in disassembled state.
Figure 27:
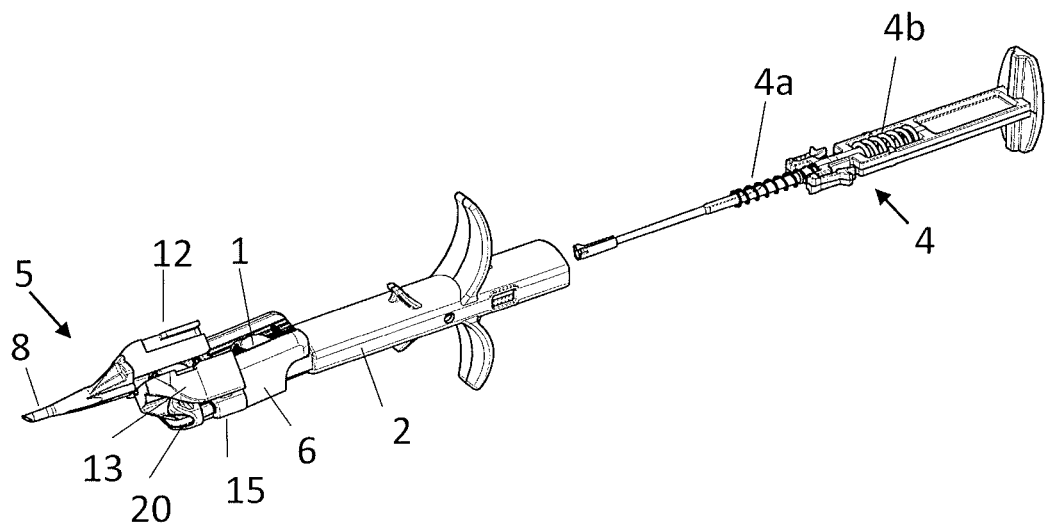
FIG. 27 shows the injector according to FIG. 26 in assembled state.

Fourth Embodiment of an Injector System for Non-Preloaded Hydrophile or Hydrophobic IOLs FIGS. 26 and 27 show a fourth embodiment of the injector system according to the invention for non-preloaded IOL 1. The present embodiment is similar to the embodiment depicted in FIGS. 1 and 2. Only the differences will be discussed herein, while corresponding elements are indicated with corresponding reference numerals. The embodiment shown in FIGS. 26 and 27 is provided with a single plunger, the injection plunger 4. No loading pusher is provided, instead the user is required to manually push the IOL 1 from the supporting surface 6a of the lens case 6 into the folding device 5 by any convenient tool, e.g. surgical forceps. In order to allow manual displacement of the IOL 1, the lens case 6 according to this embodiment has no lid. The injection plunger 4 has a second spring 4b in addition to the first spring 4a, the spring constant k2 of the second spring 4b being higher than the spring constant k1 of the first spring 4a. The ratio of the two spring constants k1 and k2 are selected such that the first spring 4a is substantially easier to compress than the second spring 4b, whereby upon applying force to the injection plunger 4 the first spring 4a is compressed first and after the first spring is completely compressed a greater force is required to push the injection plunger 4 further in by compressing the second spring 4b. The change in the spring resistance is easily recognizable by the user (surgeon), whereby the user can differentiate between two stages which allows for better control of injection of the IOL 1. This is particularly advantageous if the injector system may be used for injecting IOLs 1 of arbitrary thickness (arbitrary diopters), whereby the required injection force depends on the thickness of the particular IOL 1, which is to be implanted. A thinner IOL 1 (of smaller diopter) is more easily pushed through the nozzle 8 whereby the soft tip 7 is less compressed before the whole of the IOL 1 exits the nozzle 8, hence the injection plunger 4 needs to be pushed in less. A thicker IOL 1 (of higher diopter), on the other hand, offers more resistance, whereby the soft tip 7 needs to be compressed more before the IOL 1 is completely pushed out of the nozzle 8, meaning that the injection plunger 4 needs to be pushed further in. By ensuring tactile feedback between the two stages of the injection depth, the user can better select the required insertion length.

The folding device 5 of the present embodiment will be explained in more detail in connection with FIGS. 36A-36C.

Fifth Embodiment of an Injector System for Preloaded Hydrophobic IOLs

Figure 28:
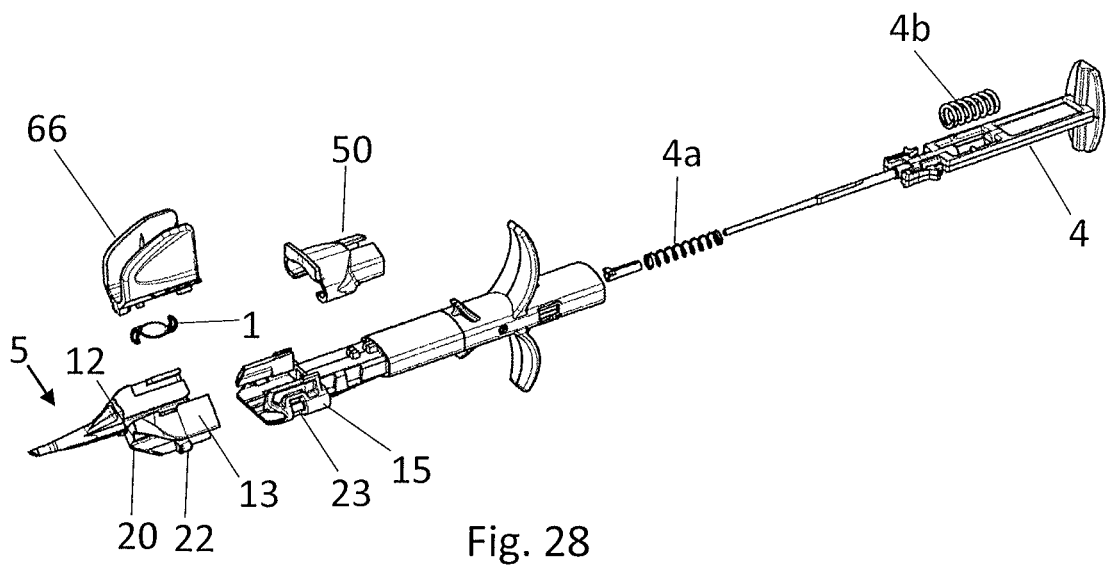
FIG. 28 shows a fourth embodiment of the injector according to the invention in disassembled state.
Figure 29:
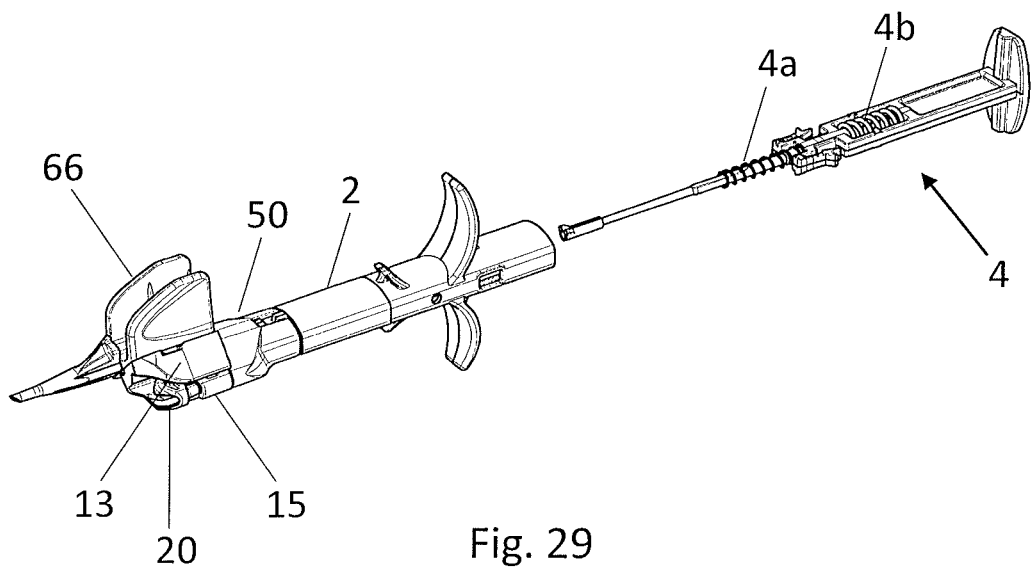
FIG. 29 shows the injector according to FIG. 28 in assembled state.

A fifth embodiment of the injector system according to the invention is depicted in FIGS. 28 and 29. Only the differences with respect to the previous embodiments are discussed herein, while corresponding elements are indicated with corresponding reference numerals. The fifth embodiment differs from all previous embodiments in that the lens case 6 is provided in the form of a lens inserter 66, and a cover element 50 is arranged on the injection body 2 at the location where the other embodiments received the lens case 6. This embodiment is also provided with a single plunger, the injection plunger 4. No loading pusher is provided, instead the lens insert 66 is used to load the IOL 1 into the receptacle 5a of the folding device 5.

Figure 30A:
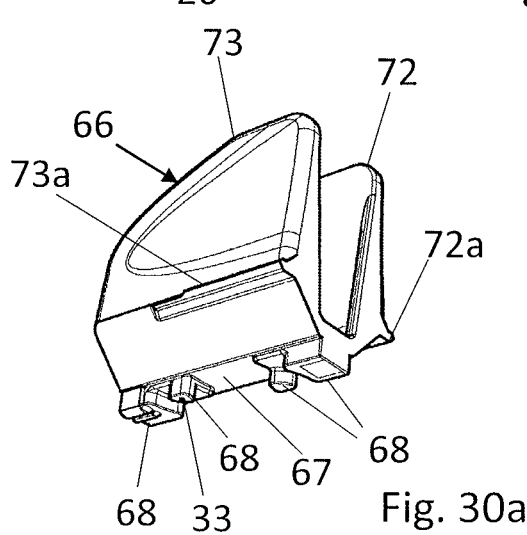
FIG. 30a is a perspective bottom view of the lens inserter of the embodiment according to FIG. 28 separately.
Figure 30B:
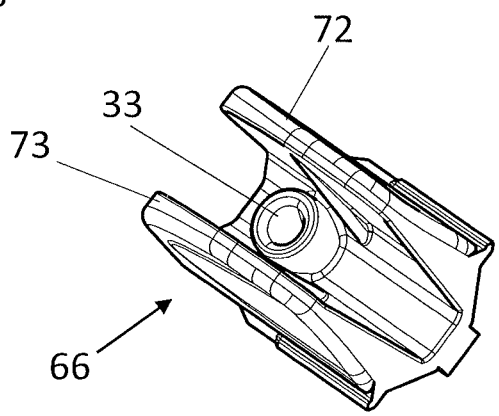
FIG. 30b is a perspective top view of the lens inserter of the embodiment according to FIG. 28 separately.

The lens inserter 66 shown in FIGS. 30a and 30b in perspective bottom and top view, respectively, has a lens receiving portion 67 wherein projections 68 are provided corresponding to the shape of the IOL 1. The lens inserter 66 has two elastically deformable side plates 72, 73, each of them being provided with a longitudinal projection 72a, 73a on their sides facing away from each other.

The lens inserter 66 is provided with a through hole 33 through which visco-elastic material can be injected into the receptacle 5a of the folding device 5 as will be explained in connection with FIG. 32. The steps of assembling the lens inserter 66 on the injector body 2 is illustrated in FIGS. 31a-31d.

Figure 31A:
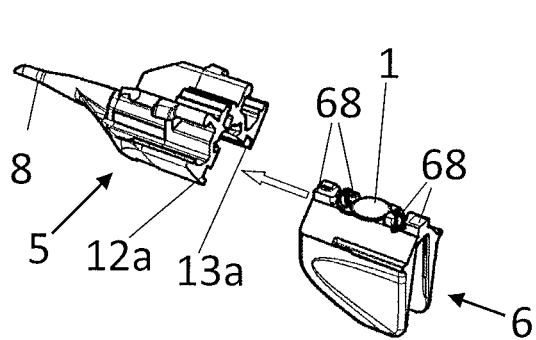
FIGS. 31a to 31d are perspective views showing the assembling steps of the preloaded injector system according to FIG. 28.
Figure 31B:
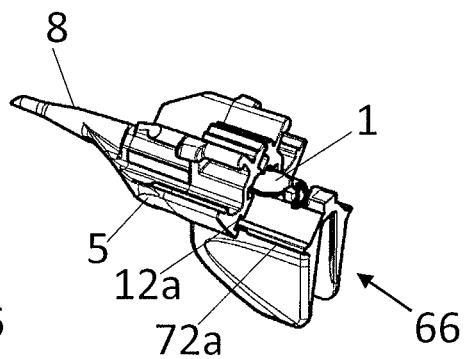
Figure 31C:
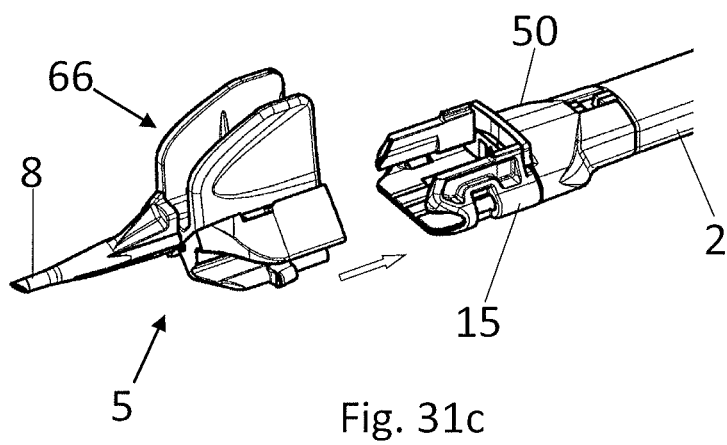
Figure 31D:
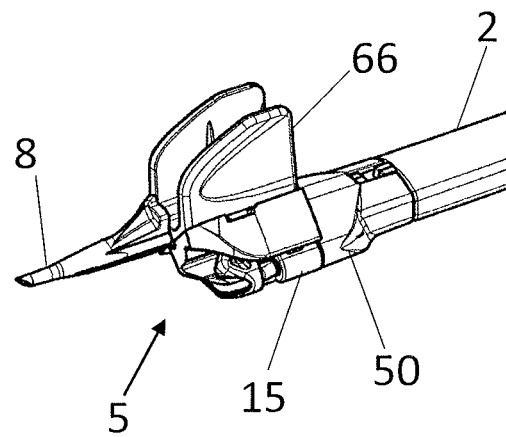

The IOL 1 is arranged on the lens receiving portion 67 between the projections 68 when the lens inserter 66 is upside down as shown in FIG. 31a. The inner surfaces of the winglets 12, 13 are provided with grooves 12a, 13a, respectively, which are dimensioned to receive the longitudinal projections 72a, 73a when the lens inserter 66 is slid into the folding device 5, also in an upside down position, as illustrated in FIGS. 31a and 31b. After this, the folding device 5 and the lens inserter 66 coupled therewith is turned back in an upright position, whereby the IOL 1, which is not supported by the lens inserter 66 from below, is received in a receptacle 5a of the folding device 5 and supported therein by the inner wall of the winglets 12, 13 forming the receptacle 5a. The folding device 5 is then inserted into the receiver 15 provided for the folding device 5 on the injector body 2 in the direction of the arrow indicated in FIG. 31c in order to assume the assembled position illustrated in FIG. 31d. The IOL 1 is thereby pre-loaded and the injector system is packaged and shipped with the pre-loaded IOL 1.

Figure 32:
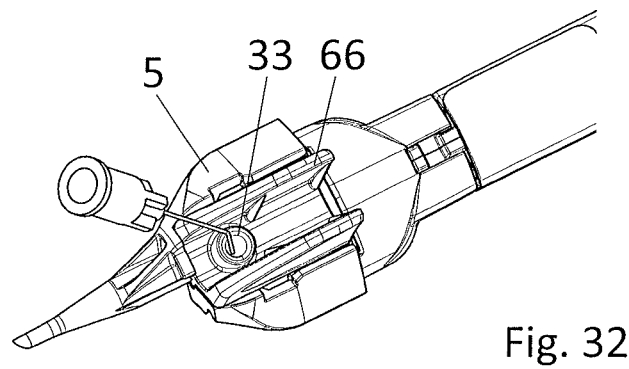
FIG. 32 is a perspective view showing the step of injecting visco-elastic material into the folding device of the injector system according to FIG. 28.

Prior to surgery the user (surgeon) injects visco-elastic material into the receptacle 5a of the folding device through the hole 33 provided in the lens inserter 66, as illustrated in FIG. 32, in order to minimize the friction between the IOL 1 and the wall of the receptacle 5a and the nozzle tube 8 when injecting the IOL 1.

Figure 33:
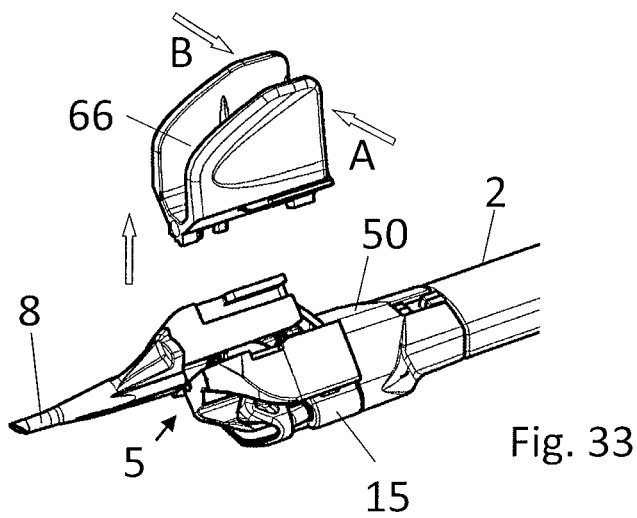
FIG. 33 is a perspective view showing the step of removing the lens inserter from the injector system according to FIG. 28.
Figure 34:
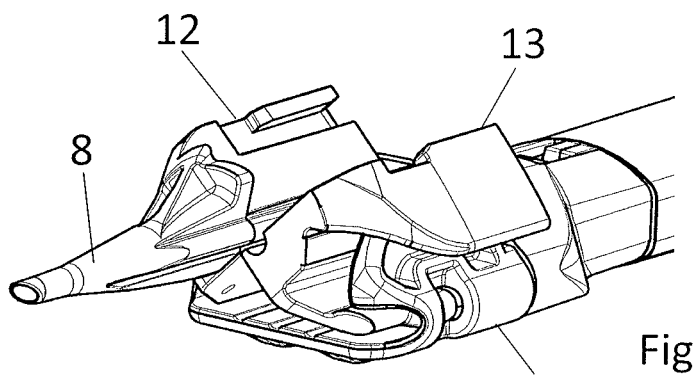
FIG. 34 is a perspective front view of a front part of the injector according to FIG. 28 with the folding device arranged in the receiver and being in an open position.
Figure 35:
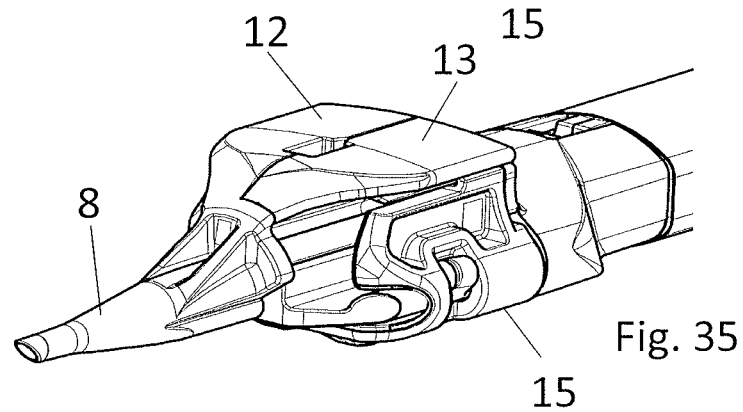
FIG. 35 is a perspective front view of the components shown in FIG. 34 wherein the folding device is in a closed position.

The user then removes the lens inserter 66 from the folding device 5 as follows. By pressing the side plates 72, 73 of the lens inserter 66 in the direction of each other as indicated by arrows A, B in FIG. 33, the longitudinal projections 72a, 73a of the side plates 72, 73 snap out of the grooves 12a, 13a, respectively, and the lens inserter 66 can be lifted from the folding device 5.

The Folding Device of the Injector Systems According to the Fourth and Fifth Embodiments FIGS. 36A, 36B and 36C schematically illustrate the structure and operating mechanism of the folding device 5 arranged in the receiver 15 of the injector system according to the fourth or fifth embodiment. The folding device 5 is shown without the nozzle tube 8. The structural elements of the present folding device 5 and receiver 15 are similar to the embodiment shown in FIGS. 9A, 9B, 9C, therefore corresponding elements are referenced by the same reference numerals.

Similarly to the previous embodiment, the folding device 5 of the present embodiment comprises a pair of co-acting winglets 12, 13 pivotable between an open position and a closed position, together defining a hinge axis 14 and a receptacle 5a for the IOL 1. Each winglet 12, 13 having an outwardly extending, unitary leg portion 20 defining a base plane 20a that includes the hinge axis 14. The base planes 20a are situated at an angle relative to one another, preferably approximately right angle when the winglets are in the open position (FIG. 36A) and the base planes 20a merge into a single plane when the winglets 12, 13 are in the closed position (FIG. 36C).

Each leg portion 20 is provided with a motion limiting protuberance 29, 30 extending from the base plane 20a. The protuberances 29, 30 abut one another when the winglets 12, 13 are in the open position. Preferably, mating elements 51, 52 (e.g. a protrusion and a corresponding groove) are provided on abutting surfaces of the protuberances 29, 30, respectively, which provide a snap fit connection between the protuberances 29, 30 when the winglets 12, 13 are in the open position as illustrated in FIG. 36A. The mating elements 51, 52 are dimensioned such that the snap fit connection is sufficient to prevent the winglets 12, 13 from closing and the folding device 5 from sliding down to the bottom of the receiver 15 under its own weight, however the snap fit connection is easy to open when a user applies force on the winglets 12, 13 in order to pivot the winglets 12, 13 toward the closed position.

The folding device 5 is arranged in the receiver 15 of the injector body 2. The receiver 15 has a base portion 151 provided with a base opening 152. The leg portion 20 of each winglet 12, 13 is supported and guided by the base portion 151 of the receiver 15 as the winglets 12, 13 are pivoted from the open to the closed position whereby the leg portions 20 slide away from each other within the two side recesses 21 of the receiver 15. When the winglets 12, 13 are completely closed the base planes 20a merge into a single plane which comes in contact with the internal side of the base portion 151 of the receiver 15. In this position the protuberances 29, 30 of each leg portion 20 extends through the base opening 152 of the receiver 15 as can be seen in FIG. 36C.

An upper edge of the receiver 15 and an external surface of an upper portion of each winglet 12, 13 are provided with co-acting flanges 19, 53, forming a snap-fit connection when the winglets 12, 13 reach their fully closed position (FIG. 36C). The co-acting flanges 19, 53 prevent the winglets 12, 13 from re-opening once they reach the closed position in order to ensure unhindered injection of the IOL 1.

As illustrated in FIGS. 36A-36C as the winglets 12, 13 are progressively closed the shape of the receptacle 5a formed between the winglets 12, 13 progressively changes so as to fold an IOL 1 placed therein and progressively descends from the level of the loading plane 16 to the level of the injection plane 17. In the closed position the cross-section of the receptacle 5a corresponds to the cross-section of the soft tip 7 of the injection plunger 4. The injection plunger 4 is arranged such that its longitudinal axis lies in the injection plane 17 so as to traverse the receptacle 5a of the folding device 5 when the folding device 5 is received in the receiver 15 and the winglets 12, 13 are in the closed position.

Operating the Injector Systems According to the Fourth and Fifth Embodiments

Use of the injector according to FIGS. 26 and 27 differs from the above described use of the injector according to FIGS. 1 and 2 in that the lens case 6 is not closed by a lid and the user is required to manually push the IOL 1 from the supporting surface 6a of the lens case 6 into the loading channel 5a of the open folding device 5 by any convenient tool, e.g. forceps.

Use of the injector according to FIGS. 28 and 29 differs from the use of the other embodiments in that the lens inserter 66 is used to insert the IOL 1 into the loading channel 5a of the open folding device 5 as described above.

Although preferred embodiments of the present invention have been illustrated in the accompanying drawings and described in the foregoing detailed description, it is understood that the invention is not limited to the disclosed embodiment but is capable of numerous rearrangements, modifications, and substitutions, for example swop of recesses and protrusions on cooperating parts of the injector system without departing from the invention.

The invention claimed is:

1. A folding device for an intraocular lens, IOL, which comprises,
    a pair of co-acting winglets pivotable between an open position and a closed position, and together defining a hinge axis and a receptacle for the IOL;
    each winglet having an outwardly extending, unitary leg portion defining a base plane that includes the hinge axis; and
    a motion limiting protuberance on each said leg portion extending from the base plane;
    the base planes being situated at an angle relative to one another and the protuberances abutting one another when the winglets are in the open position, and the base planes merging into a single plane when the winglets are in the closed position.

2. The folding device according to claim 1, wherein the base planes are situated at a right angle relative to one another when the winglets are in the open position.

3. The folding device according to claim 1, wherein one of the pair of winglets is provided with a nozzle tube having an inlet opening, and in the closed position of the winglets the inlet opening of the nozzle tube is in communication with the receptacle.

4. The folding device according to claim 3, wherein the receptacle has a first cross-section at an end adjacent the nozzle tube in the open position of the winglets and has a second cross section at said end in the closed position of the winglets such that the second cross section is completely covered by the inlet opening of the nozzle tube.

5. The folding device according to claim 1, wherein mating elements are provided on abutting surfaces of the protuberances, the mating elements providing a snap fit connection between the protuberances when the winglets are in the open position.

6. An injector system for injecting an intraocular lens (IOL), comprising an injector body and a folding device for the IOL removably positioned in the injector body,
    wherein the folding device includes a pair of co-acting winglets connected to one another along a hinge joint which defines a hinge axis therebetween, the winglets being pivotable about the hinge axis between an open position and a closed position, and together defining an open channel and a receptacle for the IOL;
each said winglet having an outwardly extending, unitary leg portion defining a base plane that includes the hinge axis and a motion limiting protuberance on each said leg portion extending from the base plane;

said base planes of the winglets being situated at an angle relative to one another, and said protuberances abutting one another when the winglets are in the open position and merging into a single plane when the winglets are in the closed position; and wherein the injector body includes a receiver for the folding device and an injector plunger, the receiver having a base portion defining a base opening, the base portion abutting said base planes and the protuberances of each said leg portion extending through said base opening when the folding device is positioned in the receiver and the winglets are in the closed position, and the injector plunger is operably associated with the receiver, aligned with the open channel and arranged to traverse the receptacle of the folding device when the folding device is received in the receiver and the winglets are in the closed position.

7. The injector system according to claim 6, wherein the protuberances are positioned on each said leg portion of the folding device so as to block the injector plunger when the folding device is received in the receiver and the winglets are in the open position.

8. The injector system according to claim 6, wherein the receiver having two opposing recesses each provided for receiving and guiding one of said leg portions from the open position of the winglets to the closed position of the winglets when the folding device is received in the receiver.

9. The injector system according to claim 6, wherein each of said leg portions is provided with a protrusion and each of said recesses of the receiver is provided with a groove for receiving one of said protrusions when the folding device is received in the receiver and the winglets are in the closed position.

10. The injector system according to claim 6, further comprising a lens case having a cavity for receiving an IOL, the injector body being provided with a lens case receiving portion for receiving said lens case, the cavity of the lens case opening into the receptacle of the folding device when the lens case is received in the lens case receiving portion of the injector body and the folding device is received in the receiver and the winglets are in the open position.

11. The injector system according to claim 6, wherein one of the pair of winglets is provided with a nozzle tube having an inlet opening, and in the closed position of the winglets the inlet opening of the nozzle tube is in communication with the receptacle.

12. The injector system according to claim 11, wherein the receptacle has a first cross-section at an end adjacent the nozzle tube in the open position of the winglets and has a second cross section at said end in the closed position of the winglets such that the second cross section is completely covered by the inlet opening of the nozzle tube.

13. The injector system according to claim 6, wherein mating elements are provided on abutting surfaces of the protuberances, the mating elements providing a snap fit connection between the protuberances when the winglets are in the open position.

14. The injector system according to claim 6, wherein the receiver has two side walls, each of said side walls being provided with a first snap lock member and an external face of each winglet being provided with a second snap lock member, the first and second snap lock members engaging each other, respectively, when the folding device is received in the receiver and the winglets are in the closed position.

15. The injector system according to claim 6, further comprising a lens inserter to be received between the winglets of the folding device when the folding device is in the open position, the lens inserter having a lens receiving portion holding the IOL in an upside-down position of the lens inserter and releasing the IOL in an upright position of the lens inserter, and the lens receiving portion is located inside the receptacle of the folding device when the lens inserter is received between the winglets of the folding device such that the lens receiving portion faces the hinge axis.

16. The injector system according to claim 6, wherein the base planes are situated at a right angle relative to one another when the winglets are in the open position.

\* \* \* \* \*